(12) United States Patent
Kim et al.

(10) Patent No.: US 12,345,521 B2
(45) Date of Patent: Jul. 1, 2025

(54) OPTICAL MEASUREMENT APPARATUS, MEASURING METHOD USING THE SAME, AND METHOD OF FABRICATING SEMICONDUCTOR DEVICE USING THE SAME

(71) Applicant: Samsung Electronics Co., Ltd., Suwon-si (KR)

(72) Inventors: Jin Yong Kim, Seoul (KR); Dae Hoon Han, Hwaseong-si (KR); Wook Rae Kim, Suwon-si (KR); Myung Jun Lee, Seongnam-si (KR); Gwang Sik Park, Hwaseong-si (KR); Sung Ho Jang, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 262 days.

(21) Appl. No.: 17/586,189

(22) Filed: Jan. 27, 2022

(65) Prior Publication Data
US 2023/0000343 A1  Jan. 5, 2023

(30) Foreign Application Priority Data
Jun. 30, 2021 (KR) .................. 10-2021-0085495

(51) Int. Cl.
*G01N 21/956* (2006.01)
*G01B 11/06* (2006.01)
(Continued)

(52) U.S. Cl.
CPC .......... *G01B 11/303* (2013.01); *G01B 11/065* (2013.01); *G01N 21/211* (2013.01); *G01N 21/956* (2013.01)

(58) Field of Classification Search
CPC ............ G01B 9/02043; G01B 9/02097; G01B 9/02098; G01B 11/06; G01B 11/0625;
(Continued)

(56) References Cited

U.S. PATENT DOCUMENTS 3,706,492 A * 12/1972 Roblin ............... G01B 9/02097
356/4.09
5,502,567 A *  3/1996 Pokrowsky ............... G01J 4/04
356/369

(Continued)

FOREIGN PATENT DOCUMENTS

EP          1598647 A1 * 11/2005 ................ G01J 3/45
KR     20210030974 A     3/2021

OTHER PUBLICATIONS

Kazuhiko Oka and Toshiaki Kaneko, "Compact complete imaging polarimeter using birefringent wedge prisms," Opt. Express 11, 1510-1519 (2003) https://opg.optica.org/oe/fulltext.cfm?uri=oe-11-13-1510&id=72892 (Year: 2003).*

(Continued)

*Primary Examiner* — Dominic J Bologna
*Assistant Examiner* — Adrian Ignacio Silva
(74) *Attorney, Agent, or Firm* — Muir Patent Law, PLLC

(57) ABSTRACT

An optical measurement apparatus includes a light source unit generating and outputting light, a polarized light generating unit generating polarized light from the light, an optical system generating a pupil image of a measurement target, using the polarized light, a self-interference generating unit generating multiple beams that are split from the pupil image, and a detecting unit detecting a self-interference image generated by interference of the multiple beams with each other.

20 Claims, 19 Drawing Sheets

(51) Int. Cl.
*G01B 11/30* (2006.01)
*G01N 21/21* (2006.01)

(58) Field of Classification Search
CPC ............ G01B 2290/70; G01B 9/02065; G01B 2290/60; G01N 21/27; G01N 21/31; G01N 21/956; G01N 21/8422; G01N 21/9501; G01N 2201/1042; G06T 7/0004; G06T 2207/30148; H04N 23/60; H01L 22/12

See application file for complete search history.

(56) References Cited

U.S. PATENT DOCUMENTS

| | | | |
|---|---|---|---|
| 6,956,658 B2 | 10/2005 | Meeks et al. | |
| 7,869,057 B2 | 1/2011 | Groot | |
| 7,978,337 B2 | 7/2011 | Groot et al. | |
| 9,310,290 B2 | 4/2016 | Wang et al. | |
| 10,444,640 B2 | 10/2019 | Ravensbergen et al. | |
| 2003/0147136 A1* | 8/2003 | Pan | G02B 6/272 359/484.05 |
| 2006/0055941 A1* | 3/2006 | Meeks | G01B 11/0616 356/601 |
| 2009/0128827 A1* | 5/2009 | de Groot | G02B 21/0004 356/491 |
| 2009/0238218 A1* | 9/2009 | Yao | H01S 3/1308 372/27 |
| 2009/0262362 A1* | 10/2009 | de Groot | G01N 21/95607 356/508 |
| 2012/0069326 A1* | 3/2012 | Colonna de Lega | G01B 11/0675 356/450 |
| 2012/0224183 A1* | 9/2012 | Fay | G01B 11/2441 356/491 |
| 2017/0045349 A1 | 2/2017 | Milner et al. | |
| 2019/0113852 A1* | 4/2019 | Ravensbergen | G03F 7/70625 |
| 2022/0003535 A1* | 1/2022 | Hidaka | G01N 21/211 |
| 2022/0074848 A1* | 3/2022 | Jung | G01N 21/211 |

OTHER PUBLICATIONS

Kazuhiko Oka and Toshiaki Kaneko, "Compact complete imaging polarimeter using birefringent wedge prisms," Opt. Express 11, 1510-1519 (2003) (Year: 2003).*

Tingkui Mu, Chunmin Zhang, Qiwei Li, Lin Zhang, Yutong Wei, and Qingying Chen, "Achromatic Savart polariscope: choice of materials," Opt. Express 22, 5043-5051 (2014) (Year: 2014).*

* cited by examiner

OPTICAL MEASUREMENT APPARATUS, MEASURING METHOD USING THE SAME, AND METHOD OF FABRICATING SEMICONDUCTOR DEVICE USING THE SAME

This application claims priority to Korean Patent Application No. 10-2021-0085495, filed on Jun. 30, 2021, and all the benefits accruing therefrom under 35 U.S.C. § 119, the disclosure of which is herein incorporated by reference in its entirety.

BACKGROUND

1. Technical Field

The present inventive concept relates to an optical measurement apparatus, an optical measuring method using the same, and a method of fabricating the semiconductor device using the same. More specifically, the present inventive concept relates to an optical measurement apparatus using an ellipsometry, an optical measuring method using the same, and a method of fabricating a semiconductor device using the same.

2. Description of the Related Art

The ellipsometry is an optical technique for studying dielectric properties of a wafer. The ellipsometry is called an elliptical method, and may analyze change in polarization state of a reflected light reflected from a sample (e.g., a wafer surface) to calculate information about the sample. For example, the reflected light reflected from the sample changes in a polarization state depending on optical properties of a sample substance, a thickness of a sample layer, and the like. The ellipsometry may obtain a complex refractive index or a dielectric function tensor which is basic physical quantities of a substance, by measuring such a polarization change, and may derive information about the sample such as a form of substance, a crystal status, a chemical structure, and an electrical conductivity.

On the other hand, an imaging ellipsometry (IE) or a spectroscopic imaging ellipsometry (SIE) is a kind of ellipsometry using a broadband light source.

SUMMARY

Aspects of the present inventive concept provide an optical measurement apparatus and a method for fabricating a semiconductor device using an optical measuring method.

Aspects of the present inventive concept also provide an optical measurement apparatus in which measurement sensitivity and measurement reliability are improved.

Aspects of the present inventive concept also provide an optical measuring method in which measurement sensitivity and measurement reliability are improved.

However, aspects of the present inventive concept are not restricted to the one set forth herein. The other aspects of the present inventive concept will become more apparent to one of ordinary skill in the art to which the present inventive concept pertains by referencing the detailed description of the present inventive concept given below.

According to an aspect of the present inventive concept, there is provided a method of fabricating a semiconductor device, the method comprising generating a polarized light, generating a pupil image of a measurement target, using the polarized light, generating a self-interference image, using the pupil image, analyzing the self-interference image to measure the measurement target, and performing a semiconductor process on the measurement target. The generating of the self-interference image includes generating multiple beams that are split from the pupil image using one or more beam displacers, and making the multiple beams interfere with each other.

According to an aspect of the present inventive concept, there is provided an optical measurement apparatus comprising a light source unit generating and outputting light, a polarized light generating unit generating polarized light from the light, an optical system generating an incident beam of a pupil image of a measurement target, using the polarized light, a self-interference generating unit generating multiple beams that are split from an incident beam of the pupil image, and a detecting unit detecting a self-interference image generated by interference of the multiple beams with each other.

According to an aspect of the present inventive concept, there is provided an optical measurement apparatus comprising a light source unit generating and outputting light, a polarized light generating unit generating polarized light from the light, a first beam splitter directing the polarized light toward a measurement target and emit a reflected light reflected from the measurement target, an objective lens condensing the polarized light on the measurement target and providing an incident beam of a pupil image of the measurement target from the reflected light, a self-interference generating unit generating multiple beams that are split from the incident beam of the pupil image, and a first detecting unit detecting a self-interference image generated by interference of the multiple beams with each other. The self-interference generating unit includes a first beam displacer and a second beam displacer that generate the multiple beams, a first wave plate interposed between the first beam displacer and the second beam displacer, and an analyzer that filters a polarization state of the multiple beams.

According to an aspect of the present inventive concept, there is provided an optical measuring method comprising generating a polarized light that is incident on a measurement target, generating a pupil image of the measurement target, using an objective lens, generating multiple beams that are split from the pupil image, using one or more beam displacers, generating a self-interference image, by causing the multiple beams to interfere with each other using an analyzer, and analyzing the self-interference image to measure the measurement target.

BRIEF DESCRIPTION OF THE DRAWINGS

The above and other aspects and features of the present inventive concept will become more apparent by describing in detail exemplary embodiments thereof with reference to the attached drawings, in which.

DETAILED DESCRIPTION OF THE EMBODIMENTS

Hereinafter, an optical measurement apparatus according to the exemplary embodiment will be described referring to FIGS. 1 to 14.

Figure 1:
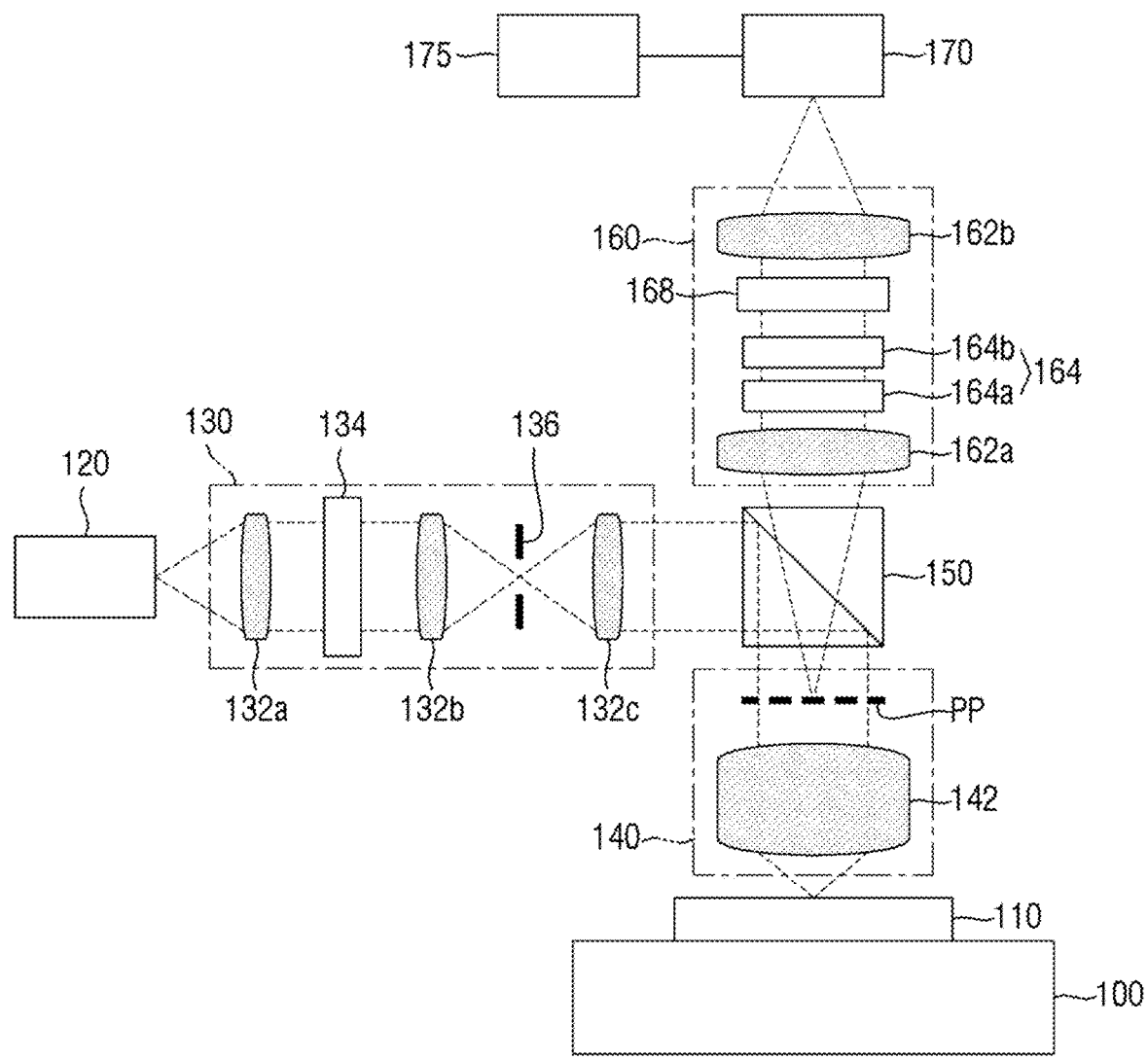
FIG. 1 is a schematic conceptual diagram for explaining an optical measurement apparatus according to some embodiments.
Figure 2:
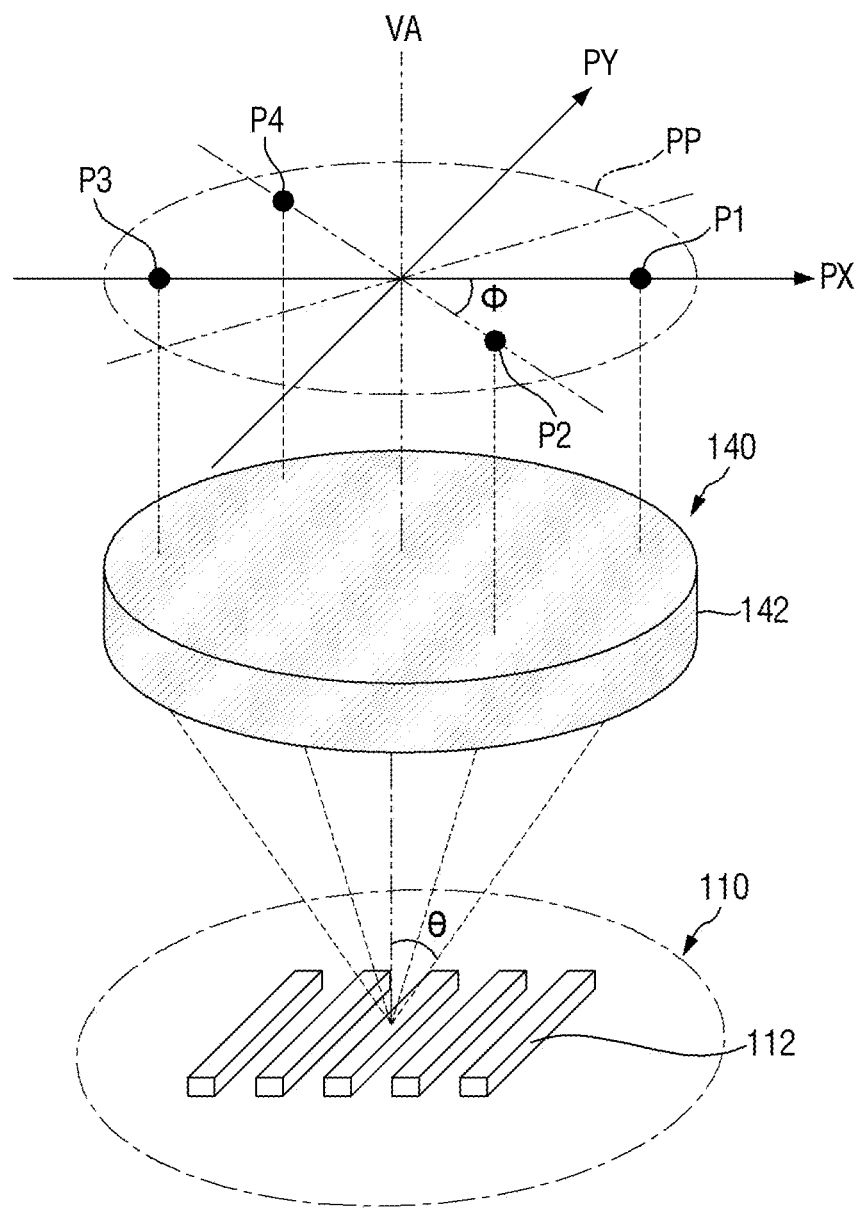
FIG. 2 is a diagram for explaining an optical system of FIG. 2.
Figure 3:
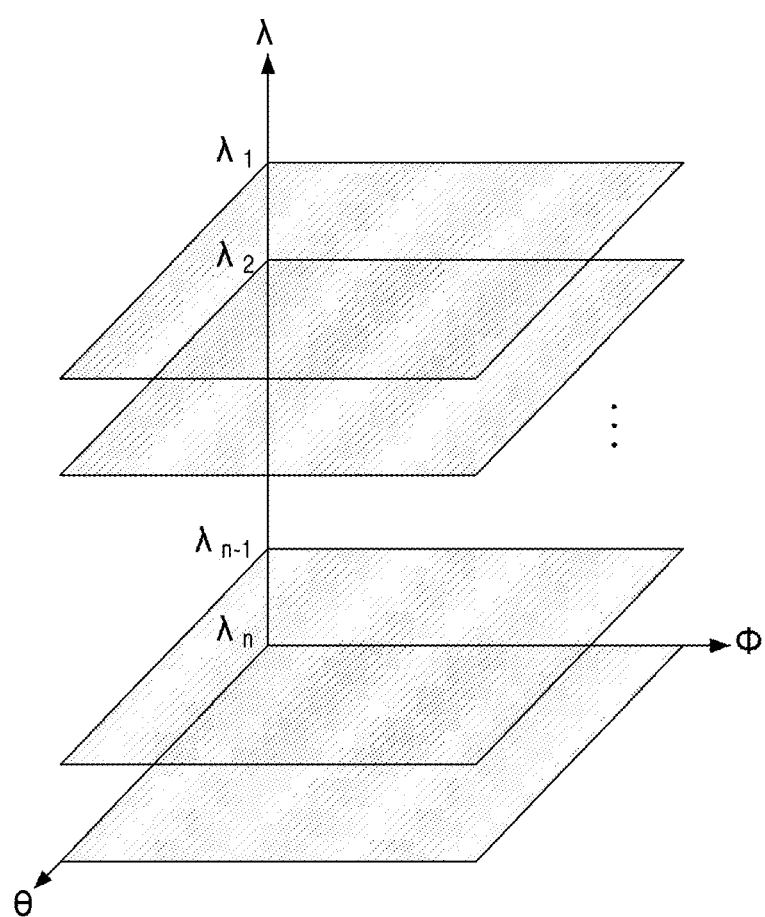
FIG. 3 is a graph for explaining the data acquired using the optical system of FIG. 2.
Figure 4:
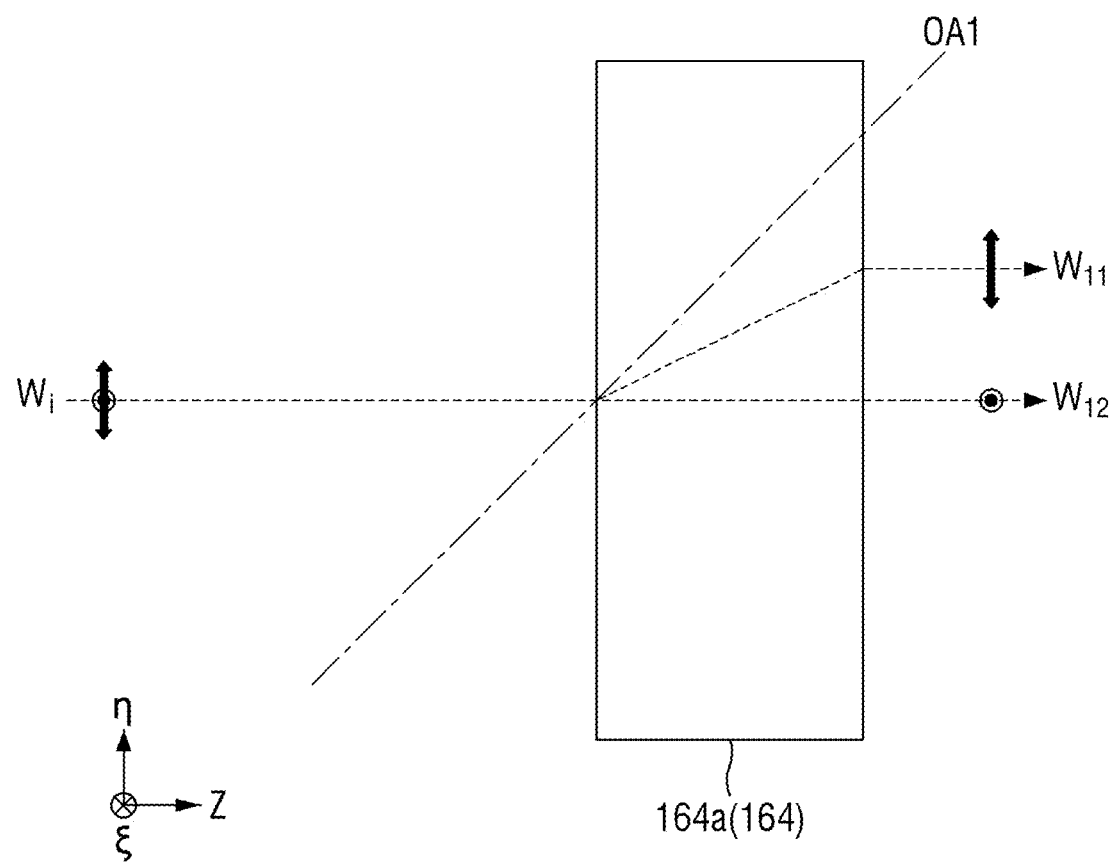
FIGS. 4 and 5 are diagrams for explaining a self-interference generating unit of FIG. 1.
Figure 5:
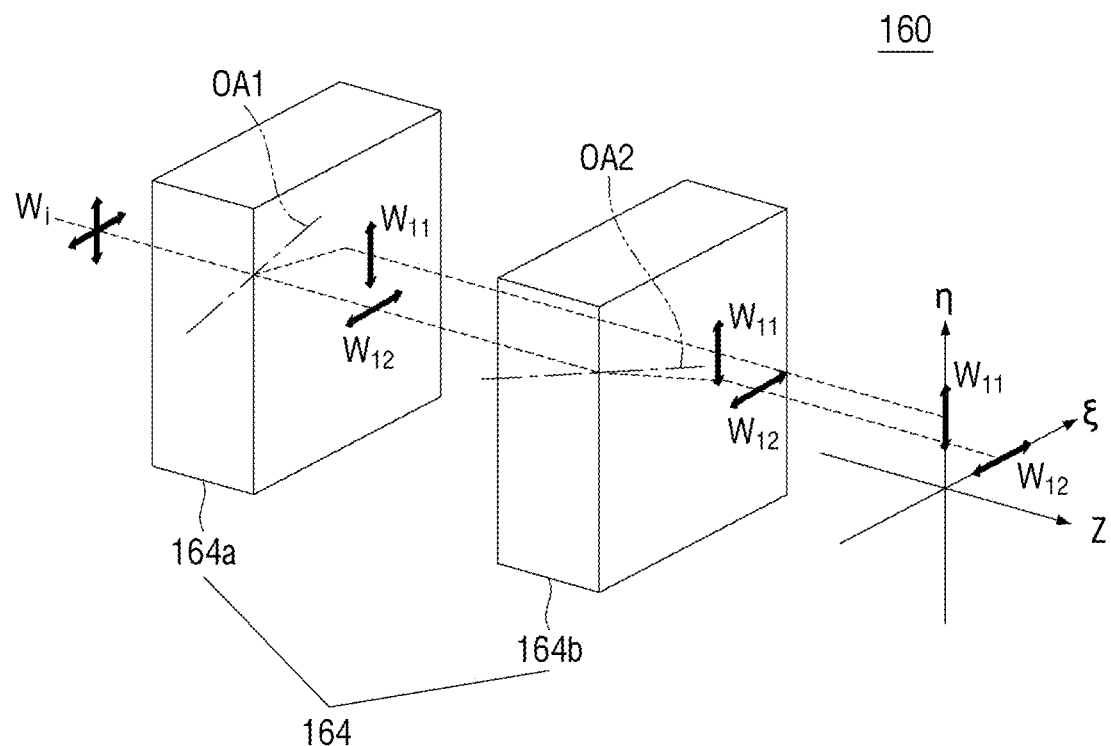

FIG. 1 is a schematic conceptual diagram for explaining an optical measurement apparatus according to some embodiments. FIG. 2 is a diagram for explaining an optical system of FIG. 2. FIG. 3 is a graph for explaining the data acquired using the optical system of FIG. 2. FIGS. 4 and 5 are diagrams for explaining a self-interference generating unit of FIG. 1.

Figure 6:
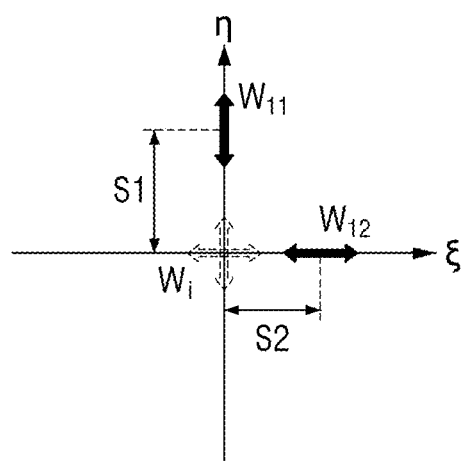
FIG. 6 is an example graph for explaining a plurality of split beams formed by the self-interference generating unit of FIG. 5.
Figure 7:
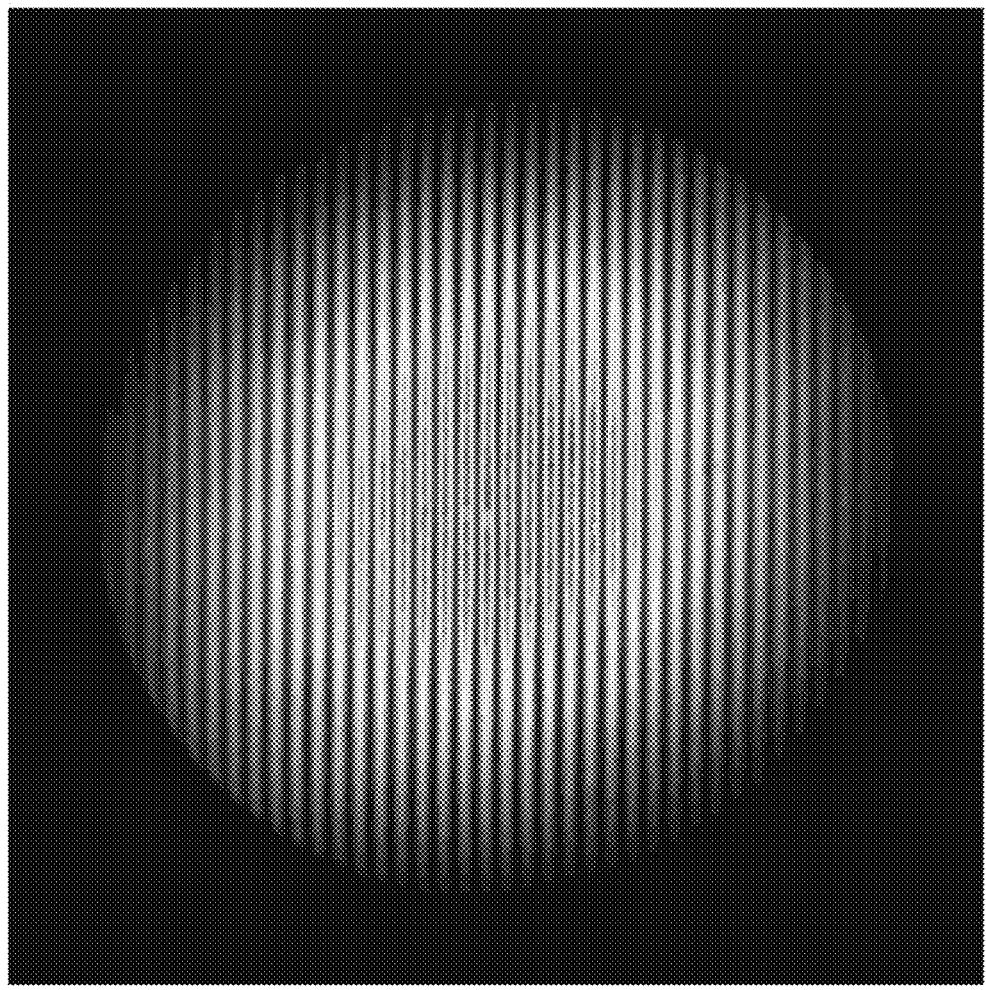
FIG. 7 is an exemplary self-interference image acquired using the optical measurement apparatus according to some embodiments.

FIG. 6 is an example graph for explaining a plurality of split beams formed by the self-interference generating unit of FIG. 5. FIG. 7 is an example self-interference image acquired using the optical measurement apparatus according to some embodiments.

Referring to FIGS. 1 to 7, the optical measurement apparatus according to some embodiment includes a light source unit 120, a polarized light generating unit 130, an optical system 140, a first beam splitter 150, a self-interference generating unit 160, a first detecting unit 170, and an image analysis unit 175.

The light source unit 120 may generate and output light. For example, the light source unit 120 may generate and output a broadband or multi-wavelength light. The broadband light may be a multicolored light including light of a plurality of wavelength bands. The broadband light may have a wide wavelength range, for example, from an ultraviolet wavelength region (e.g., about 100 nm to about 400 nm) to an infrared wavelength region (e.g., about 750 nm to about 1,000 μm). As an example, the light source unit 120 may generate and output light of the wavelength range of about 150 nm to about 2,100 nm. Terms such as "about" or "approximately" may reflect amounts, sizes, orientations, or layouts that vary only in a small relative manner, and/or in a way that does not significantly alter the operation, functionality, or structure of certain elements. For example, a range from "about 0.1 to about 1" may encompass a range such as a 0%-5% deviation around 0.1 and a 0% to 5% deviation around 1, especially if such deviation maintains the same effect as the listed range.

The light source unit 120 may be, for example, but is not limited to, a halogen lamp light source or an LED light source that produces a continuous spectrum light.

In some embodiments, the light source unit 120 may include a monochromator. The monochromator may convert and output the broadband light into monochromatic light. Here, the monochromatic light may mean light having a very short wavelength width (i.e., bandwidth) (for example, light having a wavelength bandwidth of about several nm). The monochromator may output a plurality of monochromatic lights, while sweeping with a predetermined wavelength width in a predetermined wavelength range. For example, the monochromator may sweep the broadband light in a predetermined wavelength width unit. The monochromator may include, but is not limited to, a grid or a prism that splits an incident light for each wavelength.

The polarized light generating unit 130 may polarize and output the light emitted from the light source unit 120. The polarization may include, for example, at least one of a linear polarization, a circular polarization, and an elliptical polarization. Accordingly, the polarized light generating unit 130 may generate and output the polarized light from the light source unit 120. The polarized light generating unit 130 may include, for example, first lens arrays 132a, 132b and 132c, a first polarizer 134, and an aperture 136.

The first polarizer 134 may polarize the light emitted from the light source unit 120. The first polarizer 134 may include, for example, but is not limited to, a polarizing plate and a polarizing prism.

The first lens arrays 132a, 132b and 132c may transmit the light emitted from the light source unit 120 to a measurement target 110 placed on a stage 100. For example, a first lens 132a may convert the light emitted from the light source unit 120 into a parallel light and emit the parallel light to the first polarizer 134. The polarized light generated by the first polarizer 134 may be incident on the measurement target 110 via a second lens 132b and a third lens 132c.

The aperture 136 may adjust the size of the polarized light generated by the first polarizer 134. For example, the aperture 136 may be interposed between the second lens 132b and the third lens 132c. The aperture 136 may limit a light speed diameter of polarized light emitted from the second lens 132b and provide the polarized light to the third lens 132c.

The first beam splitter 150 may direct the polarized light emitted from the polarized light generating unit 130 toward the measurement target 110, and may emit the reflected light reflected from the measurement target 110 toward the first detecting unit 170. For example, the first beam splitter 150 may reflect the polarized light emitted from the polarized light generating unit 130 and direct the polarized light toward the optical system 140. Further, the first beam splitter 150 may direct the reflected light reflected from the measurement target 110 toward the self-interference generating unit 160.

The optical system 140 may condense the polarized light emitted from the first beam splitter 150 onto the measurement target 110. For example, the optical system 140 may include an objective lens 142. The objective lens 142 may condense the polarized light emitted from the first beam splitter 150 and direct the polarized light toward the measurement target 110. The objective lens 142 may be placed so that a focus is formed at the surface of the measurement target 110. The optical system 140 may convert the reflected light reflected from the measurement target 110 into parallel lights. The optical system 140 may emit the reflected light converted into the parallel lights toward the first beam splitter 150.

The optical system 140 may provide a pupil image of the measurement target 110. The pupil image of the measurement target 110 means an image of the measurement target 110 formed at a pupil plane (PP) of the objective lens 142. Here, the pupil plane (PP) may refer to a back focal plane of the objective lens 142. For example, the objective lens 142 may form a pupil image at the pupil plane (PP) from the reflected light reflected from the measurement target 110.

For example, as shown in FIG. 2, the measurement target 110 may include a fine pattern 112. When the measurement target 110 is a wafer with the fine pattern 112, the fine pattern 112 may form various integrated circuits and wirings for a semiconductor device. The objective lens 142 may condense the polarized light and direct the polarized light toward the fine pattern 112, and may form a pupil image at the pupil plane (PP) from the reflected light reflected from the fine pattern 112.

In some embodiments, the objective lens 142 may have a high numerical aperture (NA). For example, the numerical aperture (NA) of the objective lens 142 may be about 0.9 or more. As an example, the numerical aperture (NA) of the objective lens 142 may be about 0.92 to about 0.98.

In some embodiments, the optical system 140 may move with respect to the measurement target 110. For example, the stage 100 on which the measurement target 110 is placed may operate so that the optical system 140 may move with respect to the measurement target 110. Accordingly, a pupil image on various points of the measurement target 110 may be provided.

The optical measurement apparatus according to some embodiments may acquire polarization information of various angles at the same time, by utilizing the pupil image provided from the optical system 140. Here, the polarization information may include an amplitude ratio $\Psi$, a phase difference $\Delta$, a DOP (degree of polarization), a Mueller matrix, and the like of the reflected light reflected from the measurement target 110.

In some embodiments, as shown in FIG. 2, the pupil image of the measurement target 110 formed on the pupil plane (PP) may include polarization information on various incident angles $\theta$ and azimuths $\phi$. Here, the incident angle $\theta$ may be defined as an angle formed between the polarized light which passes through a specific point (e.g., a first point P1) at the pupil plane (PP) and is incident on the measurement target 110, and a normal line VA perpendicular to an incident interface of the measurement target 110. The incident angle $\theta$ may be, for example, but is not limited to, an angle between about 0° and about 75°. The azimuth $\phi$ may be defined as an angle formed between a reference point (e.g., the first point P1) on the pupil plane (PP) and another point (e.g., a second point P2) on the pupil plane (PP), on the basis of the normal line VA. Therefore, the pupil image of the measurement target 110 may have polarization information about various angles at different points (for example, first to fourth points P1 to P4) on the pupil plane (PP). The azimuth $\phi$ may be, for example, but is not limited to, an angle between 0° and 360°. It will be understood that, although the terms first, second, third etc. may be used herein to describe various elements, components, regions, layers and/or sections, these elements, components, regions, layers and/or sections should not be limited by these terms. Unless the context indicates otherwise, these terms are only used to distinguish one element, component, region, layer or section from another element, component, region, layer or section, for example as a naming convention. Thus, a first element, component, region, layer or section discussed below in one section of the specification could be termed a second element, component, region, layer or section in another section of the specification or in the claims without departing from the teachings of the present invention. In addition, in certain cases, even if a term is not described using "first," "second," etc., in the specification, it may still be referred to as "first" or "second" in a claim in order to distinguish different claimed elements from each other.

As described above, the light source unit 120 may output a plurality of monochromatic lights, while sweeping with a predetermined wavelength width in a predetermined wavelength range. Accordingly, as shown in FIG. 3, the pupil image of the measurement target 110 may provide at least three-dimensional (the incident angle $\theta$, the azimuth $\phi$ and the wavelength $\lambda$) polarization information in a manner of one-shot. In FIG. 3, each of $\lambda_1, \lambda_2, \ldots, \lambda_{n-1}$, and $\lambda_n$ indicates an average wavelength of a corresponding monochromatic light of the plurality of monochromatic lights.

The pupil image provided from the optical system 140 may penetrate through the first beam splitter 150 and be emitted to the self-interference generating unit 160. The self-interference generating unit 160 may generate a self-interference image from the pupil image of the measurement target 110. The self-interference generating unit 160 may include, for example, second lens arrays 162a and 162b, one or more beam displacers 164, and an analyzer 168.

The beam displacer 164 may include a substance or a material having birefringence (e.g., calcite). Therefore, the beam displacer 164 may form multiple beams split from the pupil image of the measurement target 110. The plurality of split beams may interfere with each other to generate a self-interference image with respect to the pupil image. For example, the beam displacer 164 may include a first beam displacer 164a and a second beam displacer 164b that are arranged sequentially along a traveling direction Z of an incident beam $W_i$ incident on the self-interference generating unit 160. The first beam displacer 164a and the second beam displacer 164b may each have birefringence.

As shown in FIG. 4, the first beam displacer 164a may split the incident beam $W_i$ of the pupil image. The incident beam $W_i$ may include a first horizontal component beam $W_{11}$ and a first vertical component beam $W_{12}$. The first horizontal component beam $W_{11}$ is a polarized light component (that is, a p-polarized light component) of the incident beam $W_i$ that oscillates in a direction (for example, a p-polarization direction $\eta$) which is horizontal to the incident plane of the incident beam $W_i$. The first vertical component beam $W_{12}$ is a polarized light component (an s-polarized light component) of the incident beam $W_i$ that oscillates in a direction (e.g., an s-polarization direction $\xi$) that is perpendicular to the incident plane of the incident beam $W_i$.

Since the first beam displacer 164a has birefringence, the first horizontal component beam $W_{11}$ and the first vertical component beam $W_{12}$ have different refractive indexes with respect to the first beam displacer 164a. As an example, a first optical axis OA1 of the first beam displacer 164a may be at a first plane (a η-Z plane) defined by the traveling direction Z and the p-polarization direction η of the incident beam $W_i$.

The first horizontal component beam $W_{11}$ may be an extraordinary wave to the first beam displacer 164a, and the first vertical component beam $W_{12}$ may be an ordinary wave to the first beam displacer 164a. As an example, the incident beam $W_i$ may be incident vertically on the first beam displacer 164a. The first horizontal component beam $W_{11}$ may be refracted by the first optical axis OA1, and the first vertical component beam $W_{12}$ may not be refracted. For example, the first horizontal component beam $W_{11}$ may be shifted in the p-polarization direction η, and the first vertical component beam $W_{12}$ may not be shifted. Accordingly, the first beam displacer 164a may split the incident beam $W_i$ into a first horizontal component beam $W_{11}$ and a first vertical component beam $W_{12}$.

The second beam displacer 164b may shift at least one of the first horizontal component beam $W_{11}$ and the first vertical component beam $W_{12}$ that have passed through the first beam displacer 164a. In some embodiments, the first optical axis OA1 of the first beam displacer 164a may be different from a second optical axis OA2 of the second beam displacer 164b. For example, the first optical axis OA1 and the second optical axis OA2 may not be parallel to each other.

In some embodiments, a plane defined by the traveling direction Z of the incident beam $W_i$ and the first optical axis OA1 may be perpendicular to a plane defined by the traveling direction Z of the incident beam $W_i$ and the second optical axis OA2. As an example, as shown in FIG. 5, the first optical axis OA1 may be at the first plane (η-Z) plane defined by the traveling direction Z and the p-polarization direction η of the incident beam $W_i$. The second optical axis OA2 may be at the second plane (ξ-Z plane) defined by the traveling direction Z and the s-polarization direction ξ of the incident beam $W_i$. The p-polarization direction η of the incident beam $W_i$ may be perpendicular to the s-polarization direction ξ of the incident beam $W_i$.

The first horizontal component beam $W_{11}$ may be the ordinary wave of the second beam displacer 164b, and the first vertical component beam $W_{12}$ may be the extraordinary wave of the second beam displacer 164b. As an example, the first horizontal component beam $W_{11}$ and the first vertical component beam $W_{12}$ may each be vertically incident on the second beam displacer 164b. The first horizontal component beam $W_{11}$ may not be refracted, and the first vertical component beam $W_{12}$ may be refracted by the second optical axis OA2. The first horizontal component beam $W_{11}$ may not be shifted, and the first vertical component beam $W_{12}$ may be shifted in the s-polarization direction ξ.

Accordingly, one or more beam displacers 164 may generate the first horizontal component beam $W_{11}$ and the first vertical component beam W12 that are split from the incident beam $W_i$ and shifted from the incident beam $W_i$. For example, as shown in FIG. 6, the first horizontal component beam $W_{11}$ may be shifted by S1 from the incident beam $W_i$ in the p-polarization direction η, and the first vertical component beam $W_{12}$ may be shifted by S2 from the incident beam $W_i$ in the s-polarization direction ξ.

The second lens arrays 162a and 162b transmit the pupil image of the measurement target 110 provided from the optical system 140 to the first detecting unit 170. For example, a fourth lens 162a may convert the light emitted from the first beam splitter 150 into parallel lights and emit the parallel lights to the beam displacer 164. Multiple beams (for example, the first horizontal component beam $W_{11}$ and the first vertical component beam $W_{12}$) which are split by the beam displacer 164 may be incident on the first detecting unit 170 via a fifth lens 162b. The fifth lens 162b may condense the multiple beams emitted from the beam displacer 164 on the first detecting unit 170.

The analyzer 168 may be interposed between the beam displacer 164 and the first detecting unit 170. For example, the analyzer 168 may be interposed between the second beam displacer 164b and the fifth lens 162b. The analyzer 168 may filter the polarization states of multiple beams that are split by the beam displacer 164. For example, the analyzer 168 may include a second polarizer that polarizes the multiple beams (e.g., the first horizontal component beam $W_{11}$ and the first vertical component beam $W_{12}$) which are split by the beam displacer 164. The second polarizer may include, for example, but is not limited to, a polarizing plate or a polarizing prism.

Accordingly, the analyzer 168 may cause the multiple beams split by the beam displacer 164 to interfere with each other. For example, the first horizontal component beam $W_{11}$ and the first vertical component beam $W_{12}$ may be polarized by the analyzer 168 and have the same polarization direction as each other. Accordingly, the first horizontal component beam $W_{11}$ and the first vertical component beam $W_{12}$ may be polarized to have the same polarization direction as each other and may interfere with each other to generate a self-interference image.

The first detecting unit 170 may generate a two-dimensional (2D) image of the self-interference image generated by the self-interference generating unit 160. For example, the self-interference image generated by the self-interference generating unit 160 may be an image detected at the first detecting unit 170 through the fifth lens 162b. The first detecting unit 170 may be, for example, but is not limited to, a CCD (Charge Coupled Device) camera.

As an example, a self-interference image as shown in FIG. 7 may be acquired through the first detecting unit 170. When there are two beams (for example, the first horizontal component beam $W_{11}$ and the first vertical component beam $W_{12}$) that are split from the self-interference generating unit 160, as shown in FIG. 7, the acquired self-interference image may include a line-shaped interference pattern. However, this is only an example, and the acquired self-interference image may have various patterns depending on the configuration of the self-interference generating unit 160.

The image analysis unit 175 may analyze the self-interference image acquired through the first detecting unit 170. For example, a self-interference image in the form of a two-dimensional (2D) image generated from the first detecting unit 170 may be analyzed by the image analysis unit 175. Because the self-interference image is analyzed by the image analysis unit 175, the polarization information (for example, an amplitude ratio T, a phase difference Δ, a DOP (degree of polarization), a Mueller matrix, etc.) on the pupil image of the measurement target 110 may be provided. Accordingly, the image analysis unit 175 may derive information on the measurement target 110 such as a form of substance, a crystal status (i.e., a crystallization state), a chemical structure, and an electrical conductivity.

The image analysis unit 175 may be, for example, but is not limited to, a PC (Personal Computer), a workstation, a workstation, a supercomputer, and the like equipped with an analysis process. In some embodiments, the image analysis unit 175 may be formed integrally with the first detecting unit 170 to form a part of a detector or a detection device.

In some embodiments, the image analysis unit 175 may analyze the self-interference image, using a domain transform analysis. This will be described more specifically later in the description of FIG. 16A.

As the semiconductor devices become gradually integrated, more precise measurements are desirable. Also, since correlations between measurement parameters (for example, a width of fine patterns and a depth of fine patterns) increase, high measurement sensitivity and measurement reliability are required.

The optical measurement apparatus according to some embodiments may dramatically improve the measurement sensitivity and the measurement reliability, by utilizing the pupil image and the self-interference image generated from the pupil image.

As described above, the pupil image of the measurement target 110 provided from the optical system 140 may include polarization information about various angles (for example, various incident angles θ and azimuths ϕ) at the same time. This may provide significantly improved measurement sensitivity and measurement reliability compared to an optical measurement apparatus that provides only information on one angle at a time (e.g., one incident angle at a time and one azimuth at another time).

The self-interference image of a pupil image may be generated through the self-interference generating unit 160 and may be precisely analyzed. For example, as described above, the self-interference image generated from the pupil image may be precisely analyzed through the image analysis unit 175. Using the self-interference image, an optical measurement apparatus may have significantly improved measurement sensitivity and measurement reliability, and an optical measuring method may be performed using the optical measurement apparatus.

Figure 8:
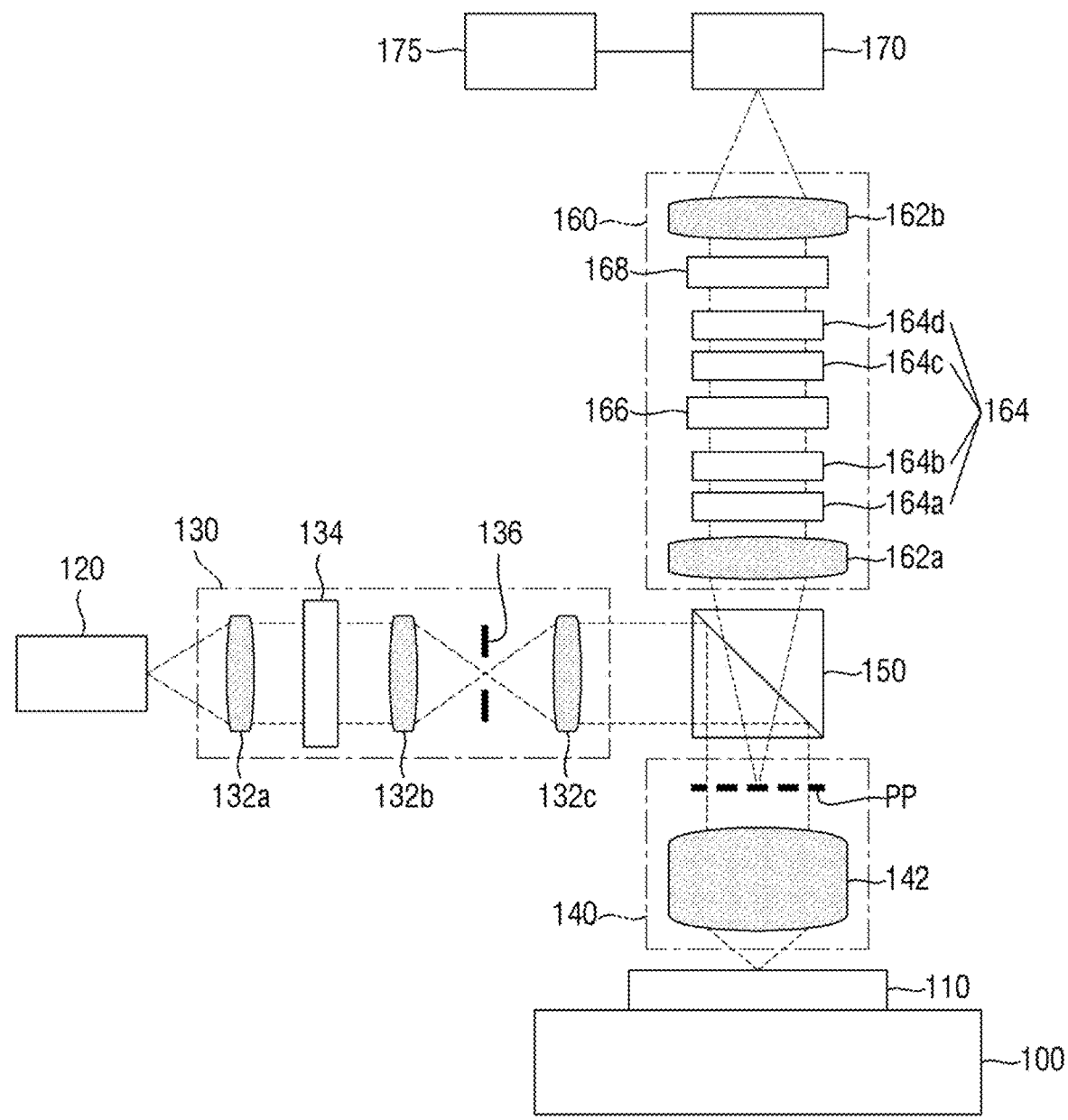
FIG. 8 is a schematic conceptual diagram for explaining the optical measurement apparatus according to some embodiments.
Figure 9:
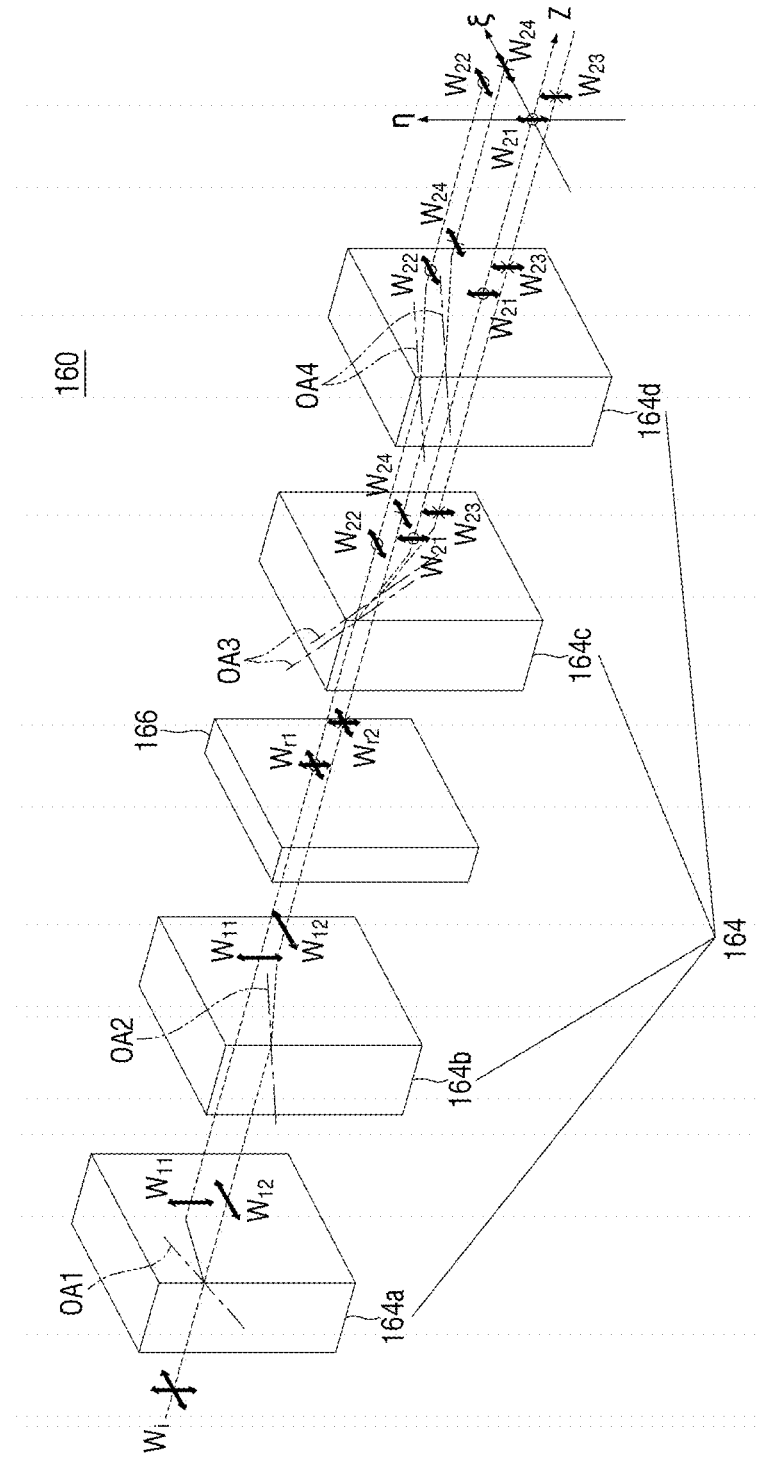
FIG. 9 is a diagram for explaining the self-interference generating unit of FIG. 8.
Figure 10:
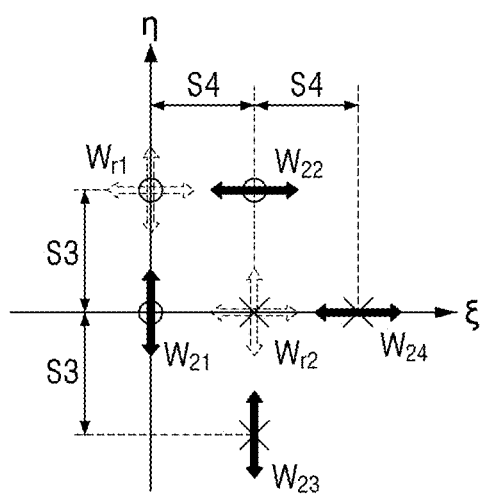
FIG. 10 is an example graph for explaining the plurality of split beams formed by the self-interference generating unit of FIG. 9.
Figure 11:
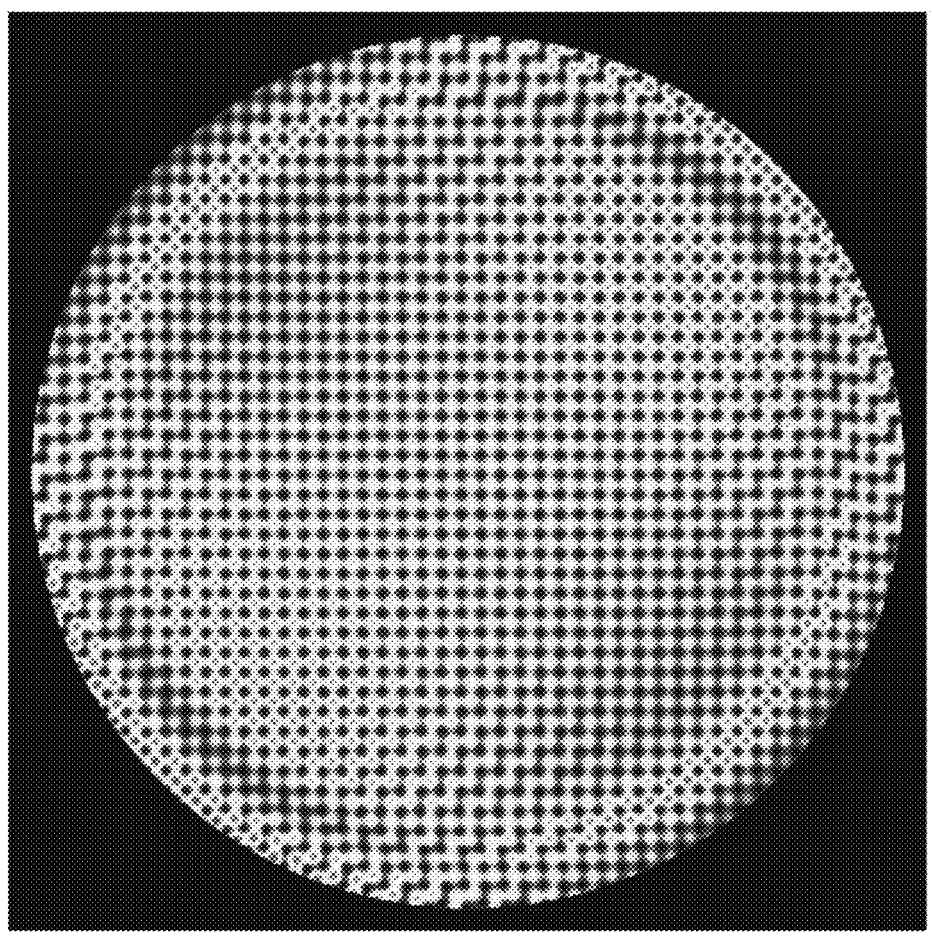
FIG. 11 is an example self-interference image obtained using the optical measurement apparatus according to some embodiments.

FIG. 8 is a schematic conceptual diagram for explaining the optical measurement apparatus according to some embodiments. FIG. 9 is a diagram for explaining the self-interference generating unit of FIG. 8. FIG. 10 is an example graph for explaining the plurality of split beams formed by the self-interference generating unit of FIG. 9. FIG. 11 is an example self-interference image obtained using the optical measurement apparatus according to some embodiments. For convenience of explanation, repeated parts of contents explained above using FIGS. 1 to 7 will be briefly described or omitted.

Referring to FIGS. 8 to 11, in the optical measurement apparatus according to some embodiments, the self-interference generating unit 160 includes a plurality of beam displacers 164 and a wave plate 166.

The plurality of beam displacers 164 may include a first beam displacer 164a, a second beam displacer 164b, a third beam displacer 164c and a fourth beam displacer 164d which are placed sequentially along the traveling direction Z of the incident beam $W_i$ that is incident on the self-interference generating unit 160. The first beam displacer 164a, the second beam displacer 164b, the third beam displacer 164c, and the fourth beam displacer 164d may each have a material of birefringence. Ordinal numbers such as "first," "second," "third," etc. may be used simply as labels of certain elements, steps, etc., to distinguish such elements, steps, etc. from one another. Terms that are not described using "first," "second," etc., in the specification, may still be referred to as "first" or "second" in a claim. In addition, a term that is referenced with a particular ordinal number (e.g., "first" in a particular claim) may be described elsewhere with a different ordinal number (e.g., "second" in the specification or another claim).

The wave plate 166 may change the polarization state of the incident beam. For example, the wave plate 166 may change the polarization direction of the incident beam. The wave plate 166 may be interposed between the second beam displacer 164b and the third beam displacer 164c. Accordingly, the wave plate 166 may change the polarization direction of the first horizontal component beam $W_{11}$ that has passed through the second beam displacer 164b to generate a first changed beam $W_{r1}$. In addition, the wave plate 166 may change the polarization direction of the first vertical component beam $W_{12}$ that has passed through the second beam displacer 164b to generate a second changed beam $W_{r2}$.

As an example, the wave plate 166 may be a half-wave plate and may have an optical axis that forms 22.5° with the polarization direction (e.g., p-polarization direction η) of the first horizontal component beam $W_{11}$ that has passed through the second beam displacer 164b. In such a case, the wave plate 166 may change the polarization direction of the first horizontal component beam $W_{11}$ that has passed through the second beam displacer 164b by 450 to generate the first changed beam $W_{r1}$. The first changed beam $W_{r1}$ may include a second horizontal component beam $W_{21}$ and a second vertical component beam $W_{22}$. The second horizontal component beam $W_{21}$ is a polarized light component (i.e., the p-polarized light component) of the first changed beam $W_{r1}$ that oscillates in a direction (e.g., p-polarization direction η) that is horizontal to the incident plane of the incident beam $W_i$, and the second vertical component beam $W_{22}$ is a polarized light component (i.e., the s-polarized light component) of the first changed beam $W_{r1}$ that oscillates in a direction (e.g., s-polarization direction ξ) that is perpendicular to the incident plane of the first changed beam $W_{r1}$.

Further, the wave plate 166 may include a half-wave plate (HWP) and may have the optical axis that forms 22.5° with the polarization direction (e.g., s-polarization direction ξ) of the first vertical component beam $W_{12}$ that has passed through the second beam displacer 164b. In such a case, the wave plate 166 may change the polarization direction of the first vertical component beam $W_{12}$ that has passed through the second beam displacer 164b by 450 to change a second changed beam $W_{r2}$. The second changed beam $W_{r2}$ may include a third horizontal component beam $W_{23}$ and a third vertical component beam $W_{24}$. The third horizontal component beam $W_{23}$ is a polarized light component (i.e., the p-polarized light component) of the second changed beam $W_{r2}$ that oscillates in a direction (e.g., p-polarization direction η) that is horizontal to the incident plane of the incident beam $W_i$, and the third vertical component beam $W_{24}$ is a polarized light component (i.e., the s-polarized light component) of the second changed beam $W_{r2}$ that oscillates in a direction e.g., s-polarization direction ξ) that is perpendicular to the incident plane of the second changed beam $W_{r2}$.

Since the third beam displacer 164c has a material of birefringence, the second horizontal component beam $W_{21}$ and the second vertical component beam $W_{22}$ have different refractive indexes with respect to the third beam displacer 164c. The third horizontal component beam $W_{23}$ and the third vertical component beam $W_{24}$ may have different refractive indexes with respect to the third beam displacer 164c. As an example, the third optical axis OA3 of the third beam displacer 164c may be at a first plane (q-Z plane) defined by the traveling direction Z and the p-polarization direction η of the incident beam $W_i$.

The second horizontal component beam $W_{21}$ and the third horizontal component beam $W_{23}$ may be extraordinary waves of the third beam displacer 164c, and the second vertical component beam $W_{22}$ and the third vertical component beam $W_{24}$ may be ordinary waves of the third beam displacer 164c. As an example, the first changed beam $W_{r1}$ and the second changed beam $W_{r2}$ may be vertically incident on the third beam displacer 164c. The second horizontal component beam $W_{21}$ and the third horizontal component beam $W_{23}$ may be refracted by the third optical axis OA3, and the second vertical component beam $W_{22}$ and the third vertical component beam $W_{24}$ may not be refracted. For example, the second horizontal component beam $W_{21}$ and the third horizontal component beam $W_{23}$ may be shifted in the p-polarization direction η, and the second vertical component beam $W_{22}$ and the third vertical component beam $W_{24}$ may not be shifted. Accordingly, the third beam displacer 164c may split the first changed beam $W_{r1}$ into the second horizontal component beam $W_{21}$ and the second vertical component beam $W_{22}$, and may split the second changed beam $W_{r2}$ into the third horizontal component beam $W_{23}$ and the third vertical component beam $W_{24}$.

The fourth beam displacer 164d may shift at least one of the second horizontal component beam $W_{21}$ and the second vertical component beam $W_{22}$ that have passed through the third beam displacer 164c, and may shift at least one of the third horizontal component beam $W_{23}$ and the third vertical component beam $W_{24}$ that have passed the third beam displacer 164c. In some embodiments, the third optical axis OA3 of the third beam displacer 164c may be different from the fourth optical axis OA4 of the fourth beam displacer 164d. For example, the third optical axis OA3 and the fourth optical axis OA4 may not be parallel to each other.

In some embodiments, a plane defined by the traveling direction Z of the incident beam $W_i$ and the third optical axis OA3 may be perpendicular to a plane defined by the traveling direction Z of the incident beam $W_i$ and the fourth optical axis OA4. As an example, as shown in FIG. 9, the third optical axis OA3 may be at the first plane (η-Z plane) defined by the traveling direction Z and the p-polarization direction η of the incident beam $W_i$. The fourth optical axis OA4 may be at the second plane (ξ-Z) plane defined by the traveling direction Z and the s-polarization direction ξ of the incident beam $W_i$.

The second horizontal component beam $W_{21}$ and the third horizontal component beam $W_{23}$ may be the ordinary waves of the fourth beam displacer 164d, and the second vertical component beam $W_{22}$ and the third vertical component beam $W_{24}$ may be extraordinary waves of the fourth beam displacer 164d. As an example, the second horizontal component beam $W_{21}$, the second vertical component beam $W_{22}$, the third horizontal component beam $W_{23}$, and the fourth vertical component beam $W_{24}$ may be each incident vertically on the fourth beam displacer 164d. The second horizontal component beam $W_{21}$ and the third horizontal component beam $W_{23}$ may not be refracted, and the second vertical component beam $W_{22}$ and the third vertical component beam $W_{24}$ may be refracted by the fourth optical axis OA4. The second horizontal component beam $W_{21}$ and the third horizontal component beam $W_{23}$ may not be shifted, and the second vertical component beam $W_{22}$ and the third vertical component beam $W_{24}$ may be shifted in the s-polarization direction ξ.

Accordingly, one or more beam displacers 164 may generate the second horizontal component beam $W_{21}$, the second vertical component beam $W_{22}$, the third horizontal component beam $W_{23}$ and the fourth vertical component beam $W_{24}$ that are split from the incident beam $W_i$ and shifted from the incident beam $W_i$. For example, as shown in FIG. 10, the second horizontal component beam $W_{21}$ may be shifted by S3 from the first changed beam $W_{r1}$ in the p-polarization direction η, and the third horizontal component beam $W_{23}$ may be shifted by S3 from the second changed beam $W_{r2}$ in the p-polarization direction n. The second vertical component beam $W_{22}$ may be shifted by S4 from the first changed beam $W_{r1}$ in the s-polarization direction, and the third vertical component beam $W_{24}$ may be shifted by S4 from the second changed beam $W_{r2}$ in the s-polarization direction ξ.

The second horizontal component beam $W_{21}$, the second vertical component beam $W_{22}$, the third horizontal component beam $W_{23}$ and the fourth vertical component beam $W_{24}$ are polarized by the analyzer 168, and may have the same polarization direction as each other. Accordingly, the polarized second horizontal component beam $W_{21}$, second vertical component beam $W_{22}$, third horizontal component beam $W_{23}$, and fourth vertical component beam $W_{24}$ may interfere with each other to generate a self-interference image.

When the self-interference generating unit 260 may split the incident beam $W_i$ into four beams (e.g., the second horizontal component beam $W_{21}$, the second vertical component beam $W_{22}$, the third horizontal component beam $W_{23}$ and the fourth vertical component beam $W_{24}$), the self-interference generating unit 160 may generate the acquired self-interference image having interference patterns in the form of a lattice, as shown in FIG. 11. However, this is only an example, and the acquired self-interference image may have various interference patterns depending on the configuration of the self-interference generating unit 160.

Figure 12:
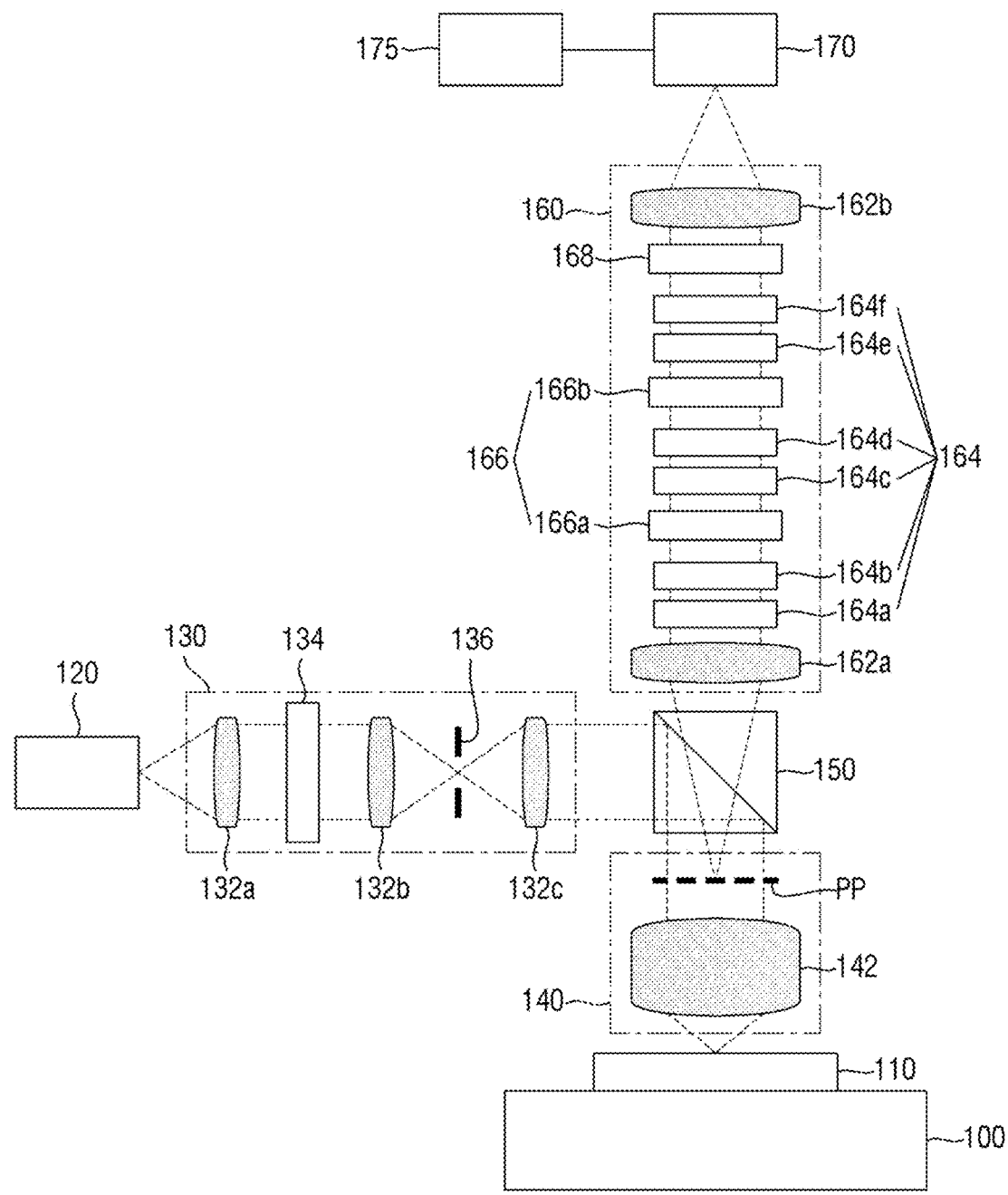
FIG. 12 is a schematic conceptual diagram for explaining an optical measurement apparatus according to some embodiments.

FIG. 12 is a schematic conceptual diagram for explaining an optical measurement apparatus according to some embodiments. For convenience of explanation, repeated parts of contents explained above using FIGS. 1 to 11 will be briefly described or omitted.

Referring to FIG. 12, in the optical measurement apparatus according to some embodiments, the self-interference generating unit 160 includes a plurality of beam displacers 164 and a plurality of wave plates 166.

The plurality of beam displacers 164 may include, for example, a first beam displacer 164a, a second beam displacer 164b, a third beam displacer 164c, a fourth beam displacer 164d, a fifth beam displacer 164e and a sixth beam displacer 164f that are sequentially arranged along the traveling direction Z of the incident beam $W_i$ incident on the self-interference generating unit 160. The first beam displacer 164a, the second beam displacer 164b, the third beam displacer 164c, the fourth beam displacer 164d, the fifth beam displacer 164e and the sixth beam displacer 164f may each have a material of birefringence.

The plurality of wave plates 166 may include, for example, a first wave plate 166a and a second wave plate 166b. The first wave plate 166a may be interposed between the second beam displacer 164b and the third beam displacer 164c, and the second wave plate 166b may be interposed between the fourth beam displacer 164d and the fifth beam displacer 164e. Each of the first wave plate 166a and the second wave plate 166b may change the polarization state of the incident beam. For example, the first wave plate 166a may change the polarization direction of the beams that have passed through the second beam displacer 164b, and the second wave plate 166b may change the polarization direction of the beams that have passed through the second beam displacer 164b.

Since the fifth beam displacer 164e and the sixth beam displacer 164f are similar to the third beam displacer 164c and the sixth beam displacer 164f described above using FIG. 8, respectively, and since the first wave plate 166a and the second wave plate 166b are each similar to the wave plate 166 described above using FIG. 8, detailed description thereof will not be provided below. Accordingly, for example, eight beams may be split from the self-interference generating unit 160.

Figure 13:
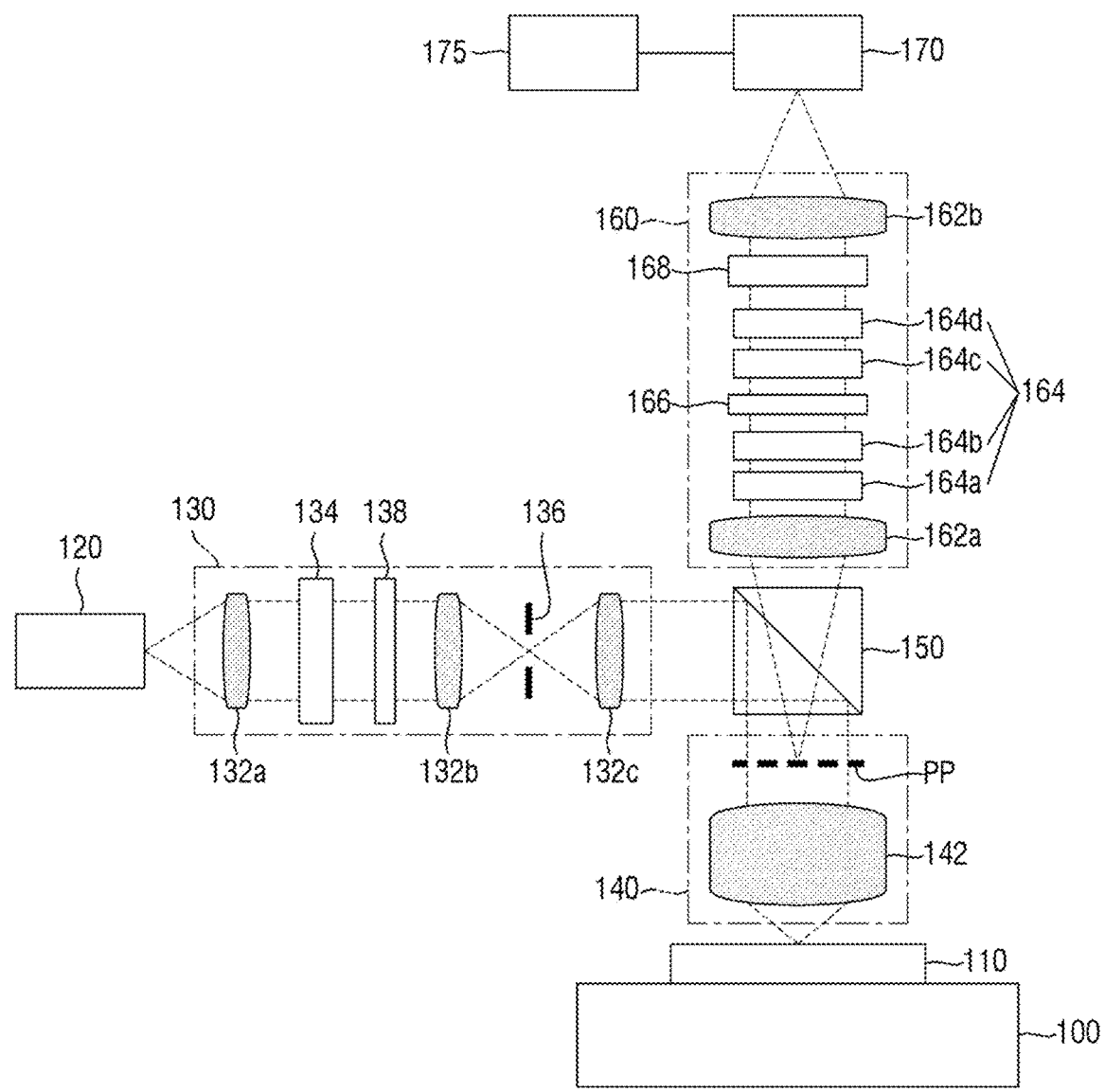
FIG. 13 is a schematic conceptual diagram for explaining an optical measurement apparatus according to some embodiments.

FIG. 13 is a schematic conceptual diagram for explaining an optical measurement apparatus according to some embodiments. For convenience of explanation, repeated parts of contents explained above using FIGS. 1 to 11 will be briefly described or omitted.

Referring to FIG. 13, in the optical measurement apparatus according to some embodiment, the polarized light generating unit 130 includes a third wave plate 138.

The third wave plate 138 may change the polarization state of the polarized light emitted from the first polarizer 134. For example, the third wave plate 138 may be interposed between the first polarizer 134 and the second lens 132b. The third wave plate 138 may change the polarization direction of the incident polarized light and provide the polarized light to the second lens 132b. The third wave plate 138 may be, for example, but is not limited to, a QWP (quarter-wave plate).

Figure 14:
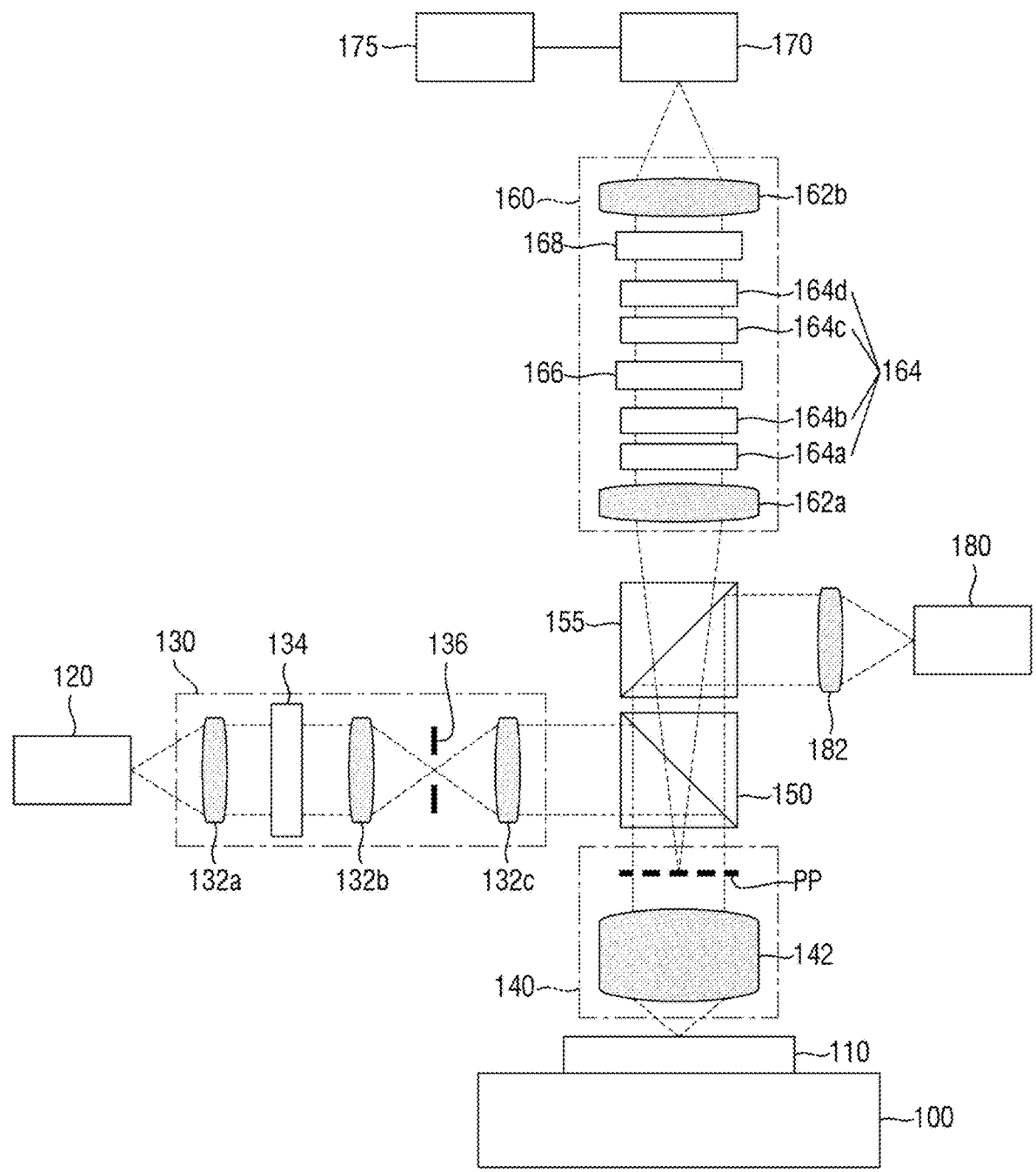
FIG. 14 is a schematic conceptual diagram for explaining an optical measurement apparatus according to some embodiments.

FIG. 14 is a schematic conceptual diagram for explaining an optical measurement apparatus according to some embodiments. For convenience of explanation, repeated parts of contents explained above using FIGS. 1 to 11 will be briefly described or omitted.

Referring to FIG. 14, the optical measurement apparatus according to some embodiments includes a second beam splitter 155 and a second detecting unit 180.

The second beam splitter 155 may direct a part of the reflected light reflected from the measurement target 110 toward the second detecting unit 180, and may emit the other part of the reflected light reflected from the measurement target 110 toward the first detecting unit 170. For example, the second beam splitter 155 may reflect a part of the reflected light reflected from the measurement target 110 and direct the part of the reflected light toward the second detecting unit 180. The second beam splitter 155 may pass the reflected light reflected from the measurement target 110 and may direct the reflected light toward the self-interference generating unit 160.

The second detecting unit 180 may generate a two-dimensional (2D) image of the reflected light reflected from the measurement target 110. For example, the reflected light reflected from the measurement target 110 may form an image at the second detecting unit 180 through the sixth lens 182. The second detecting unit 180 may be, for example, but is not limited to, a CCD camera. The two-dimensional image generated from the second detecting unit 180 may be provided as a sample image of the measurement target 110. The sample image may be used for alignment of the optical measurement apparatus to the measurement target 110 to further improve the measurement accuracy.

Hereinafter, the optical measuring method according to the example embodiment will be described referring to FIGS. 1 to 16.

Figure 15:
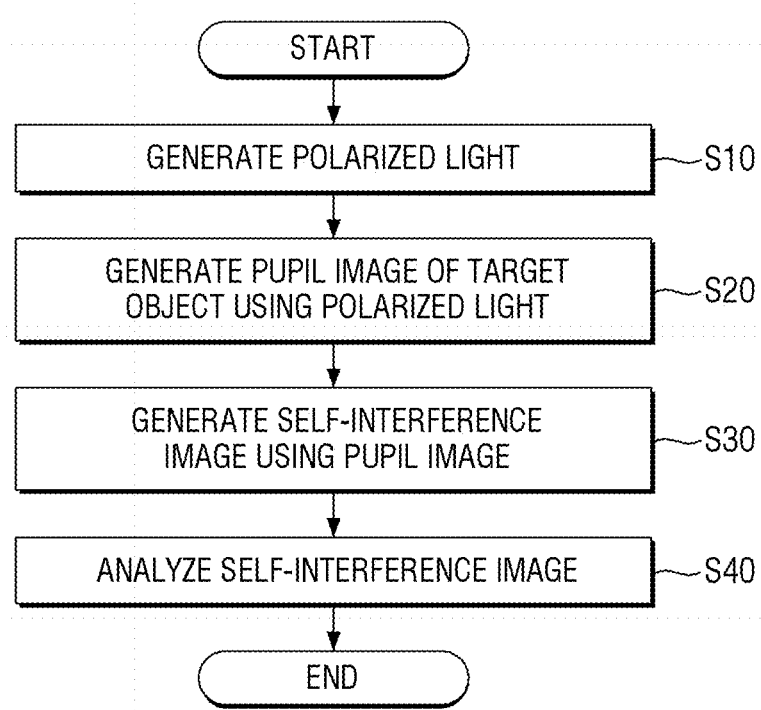
FIG. 15 is an example flowchart for explaining the optical measuring method according to some embodiments.

FIG. 15 is an example flowchart for explaining the optical measuring method according to some embodiments. For convenience of explanation, repeated parts of contents explained above using FIGS. 1 to 14 will be briefly explained or omitted.

Referring to FIG. 15, polarized light is first generated (S10).

The polarized light may include, for example, at least one of a linearly polarized light, a circularly polarized light, and an elliptically polarized light. The polarized light may be generated by, for example, the light source unit 120 and the polarized light generating unit 130 as described above using FIGS. 1 to 14.

Subsequently, a pupil image of the measurement target is generated using the polarized light (S20).

For example, an objective lens (for example, the objective lens 142 of FIGS. 1 to 14) may condense the polarized light and direct the polarized light toward the measurement target (for example, the measurement target 110 of FIGS. 1 to 14). The pupil image may be formed at the pupil plane of the objective lens. The pupil image may be generated by, for example, the optical system 140 as described above using FIGS. 1 to 14.

Subsequently, a self-interference image is generated using the pupil image (S30).

For example, multiple beams that are split from the generated pupil image may be formed. Subsequently, multiple beams may be made to interfere with each other to generate a self-interference image with respect to the pupil image. The self-interference image may be generated by, for example, the self-interference generating unit 160 described above using FIGS. 1 to 14.

Next, the self-interference image is analyzed (S40).

For example, the generated self-interference image may be analyzed to provide polarization information on the pupil image (e.g., amplitude ratio T, phase difference $\Delta$, DOP (degree of polarization), Mueller matrix, etc.). Accordingly, information on the measurement target 110 such as the form of substance, the crystal status, the chemical structure, and the electrical conductivity may be derived from the self-interference image. The self-interference image may be analyzed by, for example, the image analysis unit 175 described above using FIGS. 1 to 14.

Figure 16A:
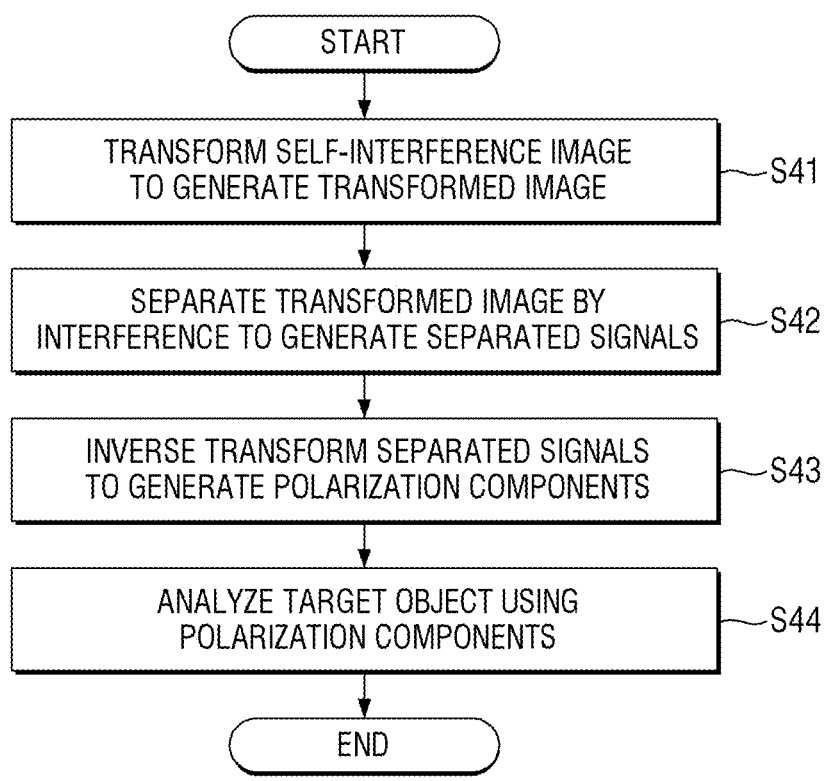
FIG. 16A is an example flowchart for explaining the steps of analyzing the self-interference image in the optical measuring method according to some embodiments.
Figure 16B:
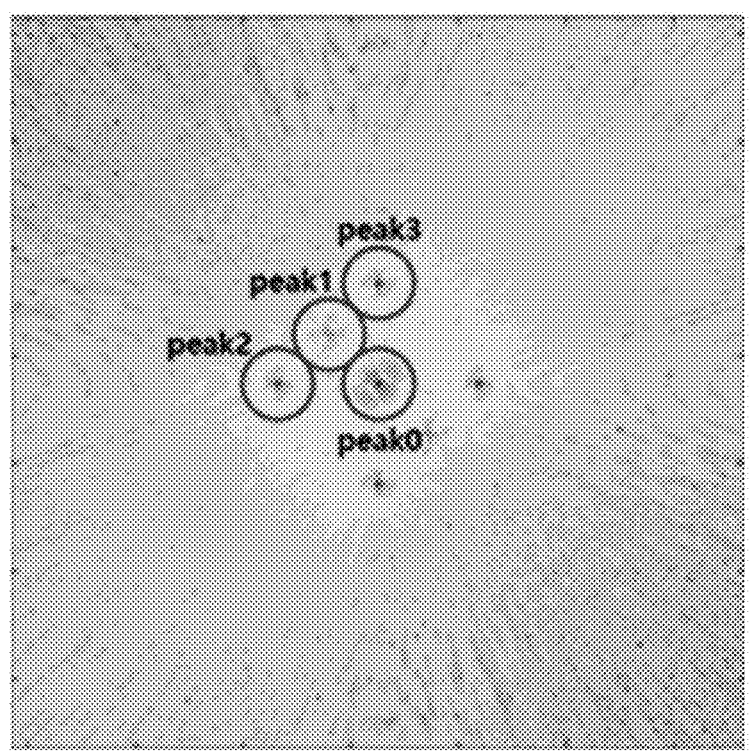
FIGS. 16B to 16D are example images for explaining the steps of analyzing the self-interference image in the optical measuring method according to some embodiments.
Figure 16C:
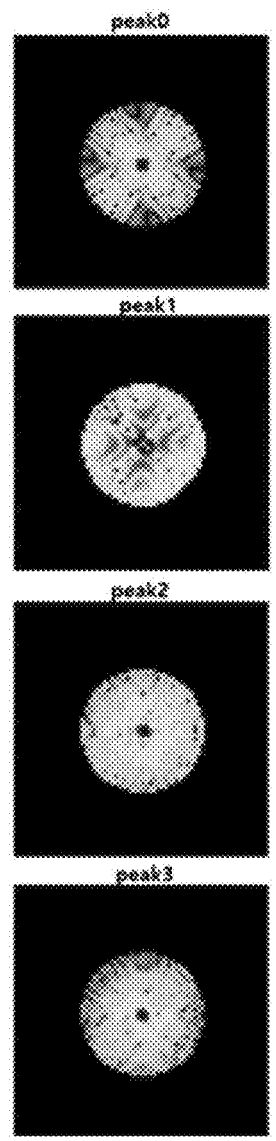
Figure 16D:
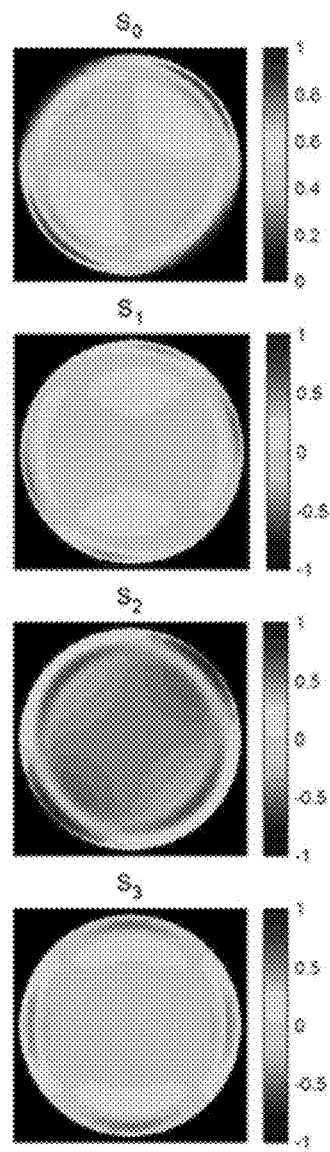

FIG. 16A is an exemplary flowchart for explaining the steps of analyzing the self-interference image in the optical measuring method according to some embodiments. FIGS. 16B to 16D are example images for explaining the steps of analyzing the self-interference image in the optical measuring method according to some embodiments. For convenience of explanation, repeated parts of contents explained above using FIGS. 1 to 15 will be briefly explained or omitted.

Referring to FIG. 16A, in the optical measuring method according to some embodiments, analyzing of the self-interference image (e.g., S40 of FIG. 15) may include utilization of domain transform analysis.

First, the generated self-interference image is transformed to generate a transformed image (S41). For example, a 2D Fourier transform may be performed on the self-interference image is transformed may be generated.

Subsequently, the generated transformed image is separated for each interference to generate a plurality of separated signals (S42). Separation of the transformed image for each interference may be performed by, for example, peak detection, filtering, centering, or the like. As an example, by performing 2D Fourier transform on the self-interference image of FIG. 11, multiple peaks may be detected, as shown in FIG. 16B. Subsequently, the multiple peaks may be separated for each peak, as shown in FIG. 16C. Accordingly, the plurality of separated signals in which the transformed images are separated for each interference component may be generated.

Subsequently, the plurality of separated signals are inversely transformed to generate polarized light components (S43). For example, a 2D inverse Fourier transform may be performed on each separated signal. Accordingly, the separated pupil image corresponding to each separated signal may be generated. Further, the polarized light components may be extracted from the generated separated pupil images. In some embodiments, the polarized light components may include Stokes vectors or Stokes parameters. As an example, by performing 2D inverse Fourier transform on the separated signals of FIG. 16C, Stokes parameters $S_0$ to $S_3$ may be generated, as shown in FIG. 16D.

Next, the measurement target is analyzed using the polarized light components (S44). For example, the polarization information (for example, an amplitude ratio T, a phase difference Δ, a DOP (degree of polarization), a Mueller matrix, etc.) on the pupil image of the measurement target (e.g., a wafer) may be acquired from the extracted polarized light components (e.g., Stokes vectors). The acquired polarization information may be compared with a theoretical formula or a library. Accordingly, information on the measurement target (e.g., a wafer) such as the form of substance, the crystal status, the chemical structure, and the electrical conductivity may be derived.

Hereinafter, a method for fabricating a semiconductor device according to an exemplary embodiment will be described referring to FIGS. 1 to 17.

Figure 17:
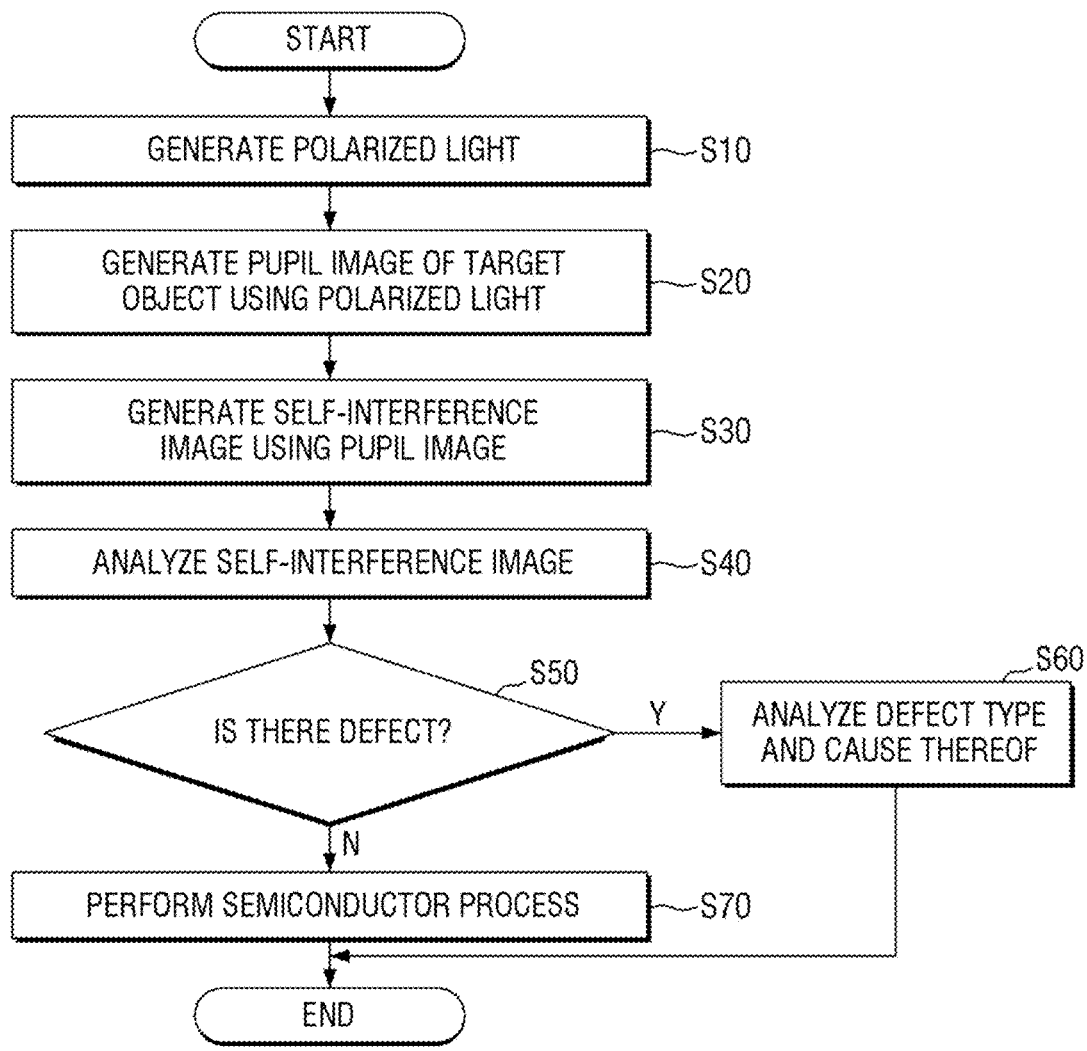
FIG. 17 is an example flowchart for explaining a method for fabricating a semiconductor device according to some embodiments.

FIG. 17 is an exemplary flowchart for explaining a method for fabricating a semiconductor device according to some embodiments. For convenience of explanation, repeated parts of contents explained above using FIGS. 1 to 16 will be briefly described or omitted.

Referring to FIG. 17, polarized light is first generated (S10), a pupil image of the measurement target is generated using the polarized light (S20), a self-interference image is generated using the pupil image (S30), and the self-interference image is analyzed (S40). Since the steps of S10 to S40 are substantially the same as those described above using FIGS. 15 and 16, detailed description thereof will not be provided below.

Next, it is determined whether there is a defect in the measurement target (S50). Whether there is a defect in the measurement target (e.g., the wafer) may be determined by measuring the measurement target. For example, it is possible to determine whether fine particles or scratches are present on the measurement target, on the basis of the result of measuring the measurement target by the use of the optical measuring method described above using FIGS. 15 and 16.

As a result of determining whether there is a defect in the measurement target (S50), if it is determined that the measurement target has a defect (Y), the type of defect and its cause are analyzed (S60). In some embodiments, a step of removing the defect through a cleaning process or the like depending on the type of defect may be performed. In some embodiments, a step of discarding the measurement target depending on the type of defect may be performed.

As a result of determining whether there is a defect in the measurement target (S50), if it is determined that there is no defect in the measurement target (N), a semiconductor process on the measurement target is performed (S70). For example, when the measurement target is a wafer, the semiconductor process on the wafer may be performed. The semiconductor process on the wafer may include, for example, but is not limited to, a vapor deposition process, an etching process, an ion process (e.g., an ion-implantation process), a cleaning process, and the like. As the semiconductor process on the wafer is performed, the integrated circuits and wirings of the semiconductor device may be formed. The semiconductor process performed on the wafer may also include a test process which is performed on the semiconductor device of a wafer level.

When the semiconductor chips are completed inside the wafer through the semiconductor process on the wafer, the wafer may be individualized into each semiconductor chip. Individualization into each semiconductor chip may be performed through a sawing process using a blade or a laser. Subsequently, a packaging process for each semiconductor chip may be performed. The packaging process may mean a process of mounting each semiconductor chip on a circuit board (e.g., a printed circuit board (PCB)) and sealing the semiconductor chips with a sealing material. Further, the packaging process may also include a process of forming a stack package by stacking a plurality of semiconductor chips in multiple levels on the circuit board, or a process of forming a POP (Package On Package) structure by stacking the stack package on the stack package. A semiconductor package may be formed through the packaging process on each semiconductor chip. The semiconductor process on the wafer may also include a test process which is performed on a semiconductor device of a package level.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims. It is therefore desired that the present embodiments be considered in all respects as illustrative and not restrictive, reference being made to the appended claims rather than the foregoing description to indicate the scope of the invention.

What is claimed is:

1. A method of fabricating a semiconductor device, the method comprising:
   generating a polarized light and illuminating the polarized light to a measurement target;
   generating a pupil image of the measurement target from the polarized light reflected from the measurement target, the pupil image including polarization information on a plurality of incident angles and a plurality of azimuths in a manner of one-shot;
   generating a self-interference image, using the pupil image;
   analyzing the self-interference image to measure the measurement target; and
   performing a semiconductor process on the measurement target depending on a result of the analyzing of the self-interference image,
   wherein the generating of the self-interference image includes:
      splitting an incident beam of the pupil image into a first component beam and a second component beam to generate multiple beams and shifting one of the first component beam and the second component beam in a first direction from a traveling direction of the incident beam, and
      receiving the first component beam and the second component beam splitted from the incident beam of the pupil image and shifting the other of the first component beam and the second component beam in a second direction from the traveling direction of the incident beam, the second direction being different from the first direction,
      making the first component beam and the second component beam interfere with each other, wherein the first direction is one of a horizontal direction and a vertical direction which are perpendicular to the traveling direction of the incident beam, and wherein the second direction is the other of the horizontal direction and the vertical direction.

2. The method of fabricating the semiconductor device of claim 1, wherein the measurement target is a wafer.

3. The method of fabricating the semiconductor device of claim 1, wherein the semiconductor process includes at least one of a vapor deposition process, an etching process, an ion process, a cleaning process, and a test process.

4. The method of fabricating the semiconductor device of claim 1, wherein making the multiple beams interfere with each other includes polarizing the multiple beams using a polarizer to have the same polarization direction as each other.

5. The method of fabricating the semiconductor device of claim 1, wherein the analyzing of the self-interference image includes utilizing a domain transform analysis.

6. The method of fabricating the semiconductor device of claim 5, wherein the domain transform analysis includes:
generating a transformed image by transforming the self-interference image using a two-dimensional Fourier transform;
separating the transformed image for each interference component to generate a plurality of interference signals;
generating a plurality of polarized light components by inversely transforming the plurality of interference signals using a two-dimensional inverse Fourier transform; and
analyzing whether the measurement target has a defect using the plurality of polarized light components.

7. The method of fabricating the semiconductor device of claim 6, wherein the plurality of polarized light components include a plurality of Stokes vectors.

8. An optical measurement apparatus comprising:
a light source unit configured to generate and output light;
a polarized light generating unit configured to generate polarized light from the light;
an optical system including an objective lens configured to receive the polarized light reflected from a measurement target and generate a pupil image of the measurement target, the pupil image including polarization information on a plurality of incident angles and a plurality of azimuths in a manner of one-shot;
a self-interference generating unit configured to receive an incident beam of the pupil image from the optical system and generate a self-interference image having an interference pattern; and
a detecting unit configured to detect the self-interference image,
wherein the generating of the self-interference image includes:
generating multiple beams including a first component beam and a second component beam that are split from the incident beam of the pupil image, at least one of the first component beam and the second component beam being shifted from the incident beam, and
making the first component beam and the second component beam interfere with each other to generate the interference pattern,
wherein the self-interference generating unit includes a first beam displacer and a second beam displacer,
wherein the first beam displacer and the second beam displacer are configured such that the second beam displacer receives the first component beam and the second component beam from the first beam displacer and the first beam displacer is configured to shift one of the first component beam and the second component beam in a first direction from the incident beam of the pupil image and the second beam displacer is configured to shift the other of the first component beam and the second component beam in a second direction from the incident beam of the pupil image, and
wherein the first direction is different from the second direction.

9. The optical measurement apparatus of claim 8, wherein the light is a broadband light, and
wherein the light source unit includes a monochromator that outputs a first monochromatic light from the broadband light.

10. The optical measurement apparatus of claim 8, wherein the incident beam of the pupil image is incident on the first beam displacer,
wherein the second component beam is a vertical component beam perpendicular to a first optical axis of the first beam displacer, and the first component beam is a horizontal component beam perpendicular to the vertical component beam, and
wherein the first beam displacer is configured to refract the horizontal component beam to shift the first component beam in the first direction.

11. The optical measurement apparatus of claim 10, wherein the second beam displacer has a second optical axis different from the first optical axis, and
wherein the second beam displacer is configured to refract the vertical component beam to shift the second component beam in the second direction.

12. The optical measurement apparatus of claim 11, wherein a first plane is defined by a traveling direction of the incident beam incident on the self-interference generating unit and the first optical axis of the first beam displacer,
wherein a second plane is defined by the traveling direction of the incident beam and the second optical axis of the second beam displacer, and
wherein the first plane is perpendicular to the second plane.

13. The optical measurement apparatus of claim 11, wherein the self-interference generating unit further includes a wave plate interposed between the first beam displacer and the second beam displacer.

14. The optical measurement apparatus of claim 8, wherein the self-interference generating unit further includes a polarizer interposed between the first beam displacer and the detecting unit.

15. An optical measurement apparatus comprising:
a light source unit configured to generate and output light;
a polarized light generating unit configured to generate polarized light from the light;
a first beam splitter configured to:
direct the polarized light toward a measurement target, and
emit a reflected light reflected from the measurement target;

an objective lens configured to:
  condense the polarized light on the measurement target, and
  generate an incident beam of a pupil image of the measurement target from the reflected light, wherein the pupil image includes polarization information on a plurality of incident angles and a plurality of azimuths in a manner of one-shot;
a self-interference generating unit configured to generate a self-interference image having an interference pattern; and
a first detecting unit configured to detect the self-interference image,
wherein the generating of the self-interference image includes:
  generating multiple beams including a first component beam and a second component beam that are split from the incident beam of the pupil image, and
  making the first component beam and the second component beam interfere with each other to generate the interference pattern, and
wherein the self-interference generating unit includes:
  a first beam displacer and a second beam displacer that generate the multiple beams, each of the first and second beam displacers including a birefringent material, wherein the first beam displacer and the second beam displacer are configured such that the second beam displacer receives the first component beam and the second component beam from the first beam displacer, wherein the first beam displacer is configured to shift one of the first component beam and the second component beam in a first direction from the incident beam of the pupil image and the second beam displacer is configured to shift the other of the first component beam and the second component beam in a second direction from the incident beam of the pupil image, wherein the first direction is different from the second direction, a first wave plate configured to receive the first component beam and the second component beam from the second beam displacer, and wherein the second beam displacer is between the first beam displacer and the first wave plate, and
  an analyzer configured to filter a polarization state of the multiple beams.

16. The optical measurement apparatus of claim 15,
wherein the first beam displacer is configured to split the incident beam incident on the self-interference generating unit into the first component beam and the second component beam,
wherein the first wave plate is configured to:
  change a polarization state of the first component beam to generate a first changed beam, and
  change a polarization state of the second component beam to generate a second changed beam, and
wherein the second beam displacer is configured to:
  split the first changed beam into a first horizontal component beam and a first vertical component beam, and
  split the second changed beam into a second horizontal component beam and a second vertical component beam.

17. The optical measurement apparatus of claim 16,
wherein the self-interference generating unit includes:
  a third beam displacer between the first beam displacer and the first wave plate, and
  a fourth beam displacer between the first wave plate and the second beam displacer,
wherein a first optical axis of the first beam displacer is different from a second optical axis of the third beam displacer, and
wherein a third optical axis of the second beam displacer is different from a fourth optical axis of the fourth beam displacer.

18. The optical measurement apparatus of claim 15, further comprising:
  an image analysis unit configured to analyze the self-interference image, using a domain transform analysis.

19. The optical measurement apparatus of claim 15, further comprising:
  a second detecting unit configured to detect the reflected light; and
  a second beam splitter configured to direct the reflected light toward the second detecting unit,
wherein the second beam splitter is between the first beam splitter and the self-interference generating unit.

20. The optical measurement apparatus of claim 15,
wherein the first wave plate is a half-wave plate.

* * * * *